(12) United States Patent
Lavelin et al.

(10) Patent No.: US 9,289,433 B2
(45) Date of Patent: Mar. 22, 2016

(54) PROTEASOME INHIBITORS AND USES THEREOF

(71) Applicant: Yeda Research and Development Co. Ltd., Rehovot (IL)

(72) Inventors: Irina Lavelin, Rehovot (IL); Varda Rotter, Rehovot (IL); Moshe Oren, Rehovot (IL); Ami Navon, Rehovot (IL); Zvi Kam, Rehovot (IL); Benjamin Geiger, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 285 days.

(21) Appl. No.: 13/872,247

(22) Filed: Apr. 29, 2013

(65) Prior Publication Data

US 2013/0225547 A1    Aug. 29, 2013

Related U.S. Application Data

(63) Continuation of application No. 13/322,453, filed as application No. PCT/IL2010/000417 on May 26, 2010, now abandoned.

(60) Provisional application No. 61/213,299, filed on May 27, 2009.

(51) Int. Cl.
| | |
|---|---|
| *A61K 31/555* | (2006.01) |
| *A61K 31/47* | (2006.01) |
| *A61K 31/522* | (2006.01) |
| *A61K 31/60* | (2006.01) |
| *A61K 33/34* | (2006.01) |
| *C07K 14/47* | (2006.01) |
| *C12N 9/64* | (2006.01) |
| *G01N 33/50* | (2006.01) |
| *A61K 31/52* | (2006.01) |

(52) U.S. Cl.
CPC ............... *A61K 31/555* (2013.01); *A61K 31/47* (2013.01); *A61K 31/52* (2013.01); *A61K 31/522* (2013.01); *A61K 31/60* (2013.01); *A61K 33/34* (2013.01); *C07K 14/4746* (2013.01); *C12N 9/6421* (2013.01); *C12Y 304/25001* (2013.01); *G01N 33/5035* (2013.01); *C07K 2319/40* (2013.01); *C07K 2319/60* (2013.01)

(58) Field of Classification Search
CPC .................................................. A61K 31/555
See application file for complete search history.

(56) References Cited

FOREIGN PATENT DOCUMENTS

| CN | 1434709 | 8/2003 | | |
|---|---|---|---|---|
| CN | 1838952 | 9/2006 | | |
| CN | 1926137 | 3/2007 | | |
| RO | 104715 | * | 9/1994 | ............. A61K 7/035 |
| WO | WO 2010/137017 | 12/2010 | | |

OTHER PUBLICATIONS

Communication Relating to the Results of the Partial International Search Dated Nov. 9, 2010 From the International Searching Authority Re. Application No. PCT/IL2010/000417.
International Preliminary Report on Patentability Dated Dec. 8, 2011 From the International Bureau of WIPO Re. Application No. PCT/IL2010/000417.
International Search Report and the Written Opinion Dated Jun. 20, 2011 From the International Searching Authority Re. Application No. PCT/IL2010/000417.
Official Action Dated Jan. 28, 2013 From the US Patent and Trademark Office Re. U.S. Appl. No. 13/322,453.
Altaf et al. "Evaluation of the Mycobacterium Smegmatis and BCG Models for the Discovery of Mycobacterium Tuberculosis Inhibitors", Tuberculosis, XP002635922, 90(6): 333-337, Nov. 2010. Abstract, Table 2.
Andreatta et al. "Use of Short-Lived Green Fluorescent Protein for the Detection of Proteasome Inhibition", BioTechniques, 30(3): 656-660, Mar. 2001.
Bence et al. "Impairment of the Ubiquitin-Proteasome System by Protein Aggregation", Science, 292(5521): 1552-1555, May 25, 2001.
Dantuma et al. "Short-Lived Green Fluorescent Proteins for Quantifying Ubiquitin/Proteasome-Dependent Proteolysis in Living Cells", Nature Biotechnology, 18: 538-543, May 2000.
Dorjsuren et al. "Chemical Library Screen for Novel Inhibitors of Kaposi's Sarcoma-Associated Herpesvirus Processive DNA Synthesis", Antiviral Research, XP025031333, 69(1): 9-23, Jan. 1, 2006.
Glover et al. "A High-Throughput Screen for Identification of Molecular Mimics of Smac/DIABLO Utilizing a Fluorescence Polarization Assay", Analytical Biochemistry, XP004447141, 320(2): 157-169, Sep. 15, 2003. p. 167, r-h Col., § 2, Fig.7.
Guedat et al. "Patented Small Molecule Inhibitors in the Ubiquitin Proteasome System", BMC Biochemistry, XP002602467, 8(Suppl. 1): S14, 12 P., Nov. 2007. Abstract, p. 1, r-h Col., § 2-p. 4, r-h Col., § 1.

(Continued)

*Primary Examiner* — Amber D Steele

(57) ABSTRACT

A method of treating a disease in which inhibiting of a proteasome is advantageous is provided. The method comprises administering to the subject a therapeutically effective amount of a compound which binds to a proteasome of a cell, the compound comprising a copper bound to a ligand, the ligand being configured such that upon binding to the proteasome, the copper interacts with cysteine 31 of a Beta2 subunit of the proteasome and further interacts with cysteine 118 of a Beta3 subunit of the proteasome, thereby treating the disease. Additional novel proteasome inhibitors are also provided as well as methods of identifying proteasome inhibitors.

4 Claims, 12 Drawing Sheets

(6 of 12 Drawing Sheet(s) Filed in Color)

(56) References Cited

OTHER PUBLICATIONS

Hoeller et al. "Targeting the Ubiquitin System in Cancer Therapy", Nature, XP002602464, 458(7237): 438-444, Mar. 26, 2009. Abstract, p. 441, l-h Col., § 4-r-h Col., § 4.

Lavelin et al. "Discovery of Novel Proteasome Inhibitors Using a High-Content Cell-Based Screening System", PLoS ONE, XP002602463, 4(12): E8503.1-E8503.9, Dec. 2009.

Moravec et al. "Cell-Based Bioluminescent Assays for the Three Protcasome Activities in a Homogeneous Format", Analytical Biochemistry, 387: 294-302, 2009.

Nickeleit et al. "Argyrin A Reveals a Critical Role for the Tumor Suppressor Protein P27[kip1] in Mediating Antitumor Activities in Response to Protasome Inhibition", Cancer Cell, 14: 23-35, Jul. 2008.

O'Keefe et al. "Nucleocytoplasmic Shuttling of P53 Is Essential for MDM2-Mediated Cytoplasmic Degradation But Not Ubiquitination", Molecular and Cellular Biology, XP002602465, 23(18): 6396-6405, Sep. 2003. Abstract, p. 6397, l-h Col., Last § -6399, 1-h col., § 1, Fig.1.

PubChem "NCI321206—Compound Summary", Database PubChem [Online], XP002602461, Retrieved From NCBI, Database Accession No. CID 4318826, Sep. 13, 2005.

PubChem "NSC310551—Substance Summary", PubChem Public Chemical Database, XP002635923, Retrieved From the Internet, Feb. 29, 2008.

Sterz et al. "The Potential of Proteasome Inhibitors in Cancer Therapy", Expert Opinion on Investigational Drugs, XP002602466, 17(6): 879-895, Jun. 2008.

Vogt et al. "Cell-Active Dual Specificity Phosphatase Inhibitors Identified by High-Content Screening", Chemistry & Biology, XP002602462, 10(8): 733-742, Aug. 2003. Figs.2, 4.

Translation of Office Action Dated Jun. 27, 2013 From the State Intellectual Property Office of the People's Republic of China Re. Application No. 201080033618.8.

Translation of Search Report Dated Jun. 27, 2013 From the Stale Intellectual Property Office of the People's Republic of China Re. Application No. 201080033618.8.

* cited by examiner

FIG. 6

| | CONTROL | NSC3907 | NSC99671 | NSC310551 | NSC321206 |
|---|---|---|---|---|---|
| Image | | | | | |
| Chemical name | - | 8-Hydroxyquinoline salicylate | 2-{2-[(1,3-dimethyl-2-oxo-6-sulfanylidene-7H-purin-8-yl)sulfanyl]ethyl}isoindole-1,3-dione | copper; [(6-methylpyridin-2-yl)methylideneamino}-[methylsulfanyl(sulfonio)methylidene]methyl)azanide | bromocopper; {dipyridin-2-ylmethylideneamino}-[methylsulfanyl(sulfonium-ylidene)methyl]azanide |
| Molecular formula | - | C16H13NO4 | C17H15N5O3S2 | C18H22CuN6S4 | C13H12BrCuN4S2 |
| Structure | | | | | |
| EC50 | - | 5 μM | 15 μM | 0.25 μM | 0.1 μM |

SEQUENCE LISTING

```
<160> NUMBER OF SEQ ID NOS: 7

<210> SEQ ID NO 1
<211> LENGTH: 360
<212> TYPE: PRT
<213> ORGANISM: Homo sapiens
<220> FEATURE:
<221> NAME/KEY: misc_feature
<223> OTHER INFORMATION: Human p53 polypeptide

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
```

```
            20                  25                  30
Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly
        355                 360

<210> SEQ ID NO 2
<211> LENGTH: 393
<212> TYPE: PRT
<213> ORGANISM: Artificial sequence
<220> FEATURE:
<223> OTHER INFORMATION: Human derived mutant p53 mutated on L319A,
      L320A and L321A

<400> SEQUENCE: 2

Met Glu Glu Pro Gln Ser Asp Pro Ser Val Glu Pro Pro Leu Ser Gln
1               5                   10                  15
```

```
Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
 50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
             100                 105                 110

Phe Leu His Ser Gly Thr Ala Lys Ser Val Thr Cys Thr Tyr Ser Pro
         115                 120                 125

Ala Leu Asn Lys Met Phe Cys Gln Leu Ala Lys Thr Cys Pro Val Gln
 130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
             165                 170                 175

Pro His His Glu Arg Cys Ser Asp Ser Asp Gly Leu Ala Pro Pro Gln
         180                 185                 190

His Leu Ile Arg Val Glu Gly Asn Leu Arg Val Glu Tyr Leu Asp Asp
 195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
             245                 250                 255

Leu Glu Asp Ser Ser Gly Asn Leu Leu Gly Arg Asn Ser Phe Glu Val
         260                 265                 270

Arg Val Cys Ala Cys Pro Gly Arg Asp Arg Arg Thr Glu Glu Glu Asn
 275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Ala Ala
305                 310                 315                 320

Ala Pro Leu Asp Gly Glu Tyr Phe Thr Leu Gln Ile Arg Gly Arg Glu
             325                 330                 335

Arg Phe Glu Met Phe Arg Glu Leu Asn Glu Ala Leu Glu Leu Lys Asp
         340                 345                 350

Ala Gln Ala Gly Lys Glu Pro Gly Gly Ser Arg Ala His Ser Ser His
 355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 3
<211> LENGTH: 392
<212> TYPE: PRT
<213> ORGANISM: Artificial sequence
<220> FEATURE:
<223> OTHER INFORMATION: R175H, L319A, L320A and L321A p53 mutant
``` polypeptide

<400> SEQUENCE: 3

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg His Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Ala Ala
305                 310                 315                 320

Ala Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser
385                 390
```

<210> SEQ ID NO 4
<211> LENGTH: 1179
<212> TYPE: DNA
<213> ORGANISM: Artificial sequence
<220> FEATURE:
<223> OTHER INFORMATION: mutant p53 coding portion of the p53-YFP
      construct

<400> SEQUENCE: 4

```
atggaggagc cgcagtcaga tcctagcgtc gagccccctc tgagtcagga aacattttca      60
gacctatgga aactacttcc tgaaaacaac gttctgtccc ccttgccgtc ccaagcaatg     120
gatgatttga tgctgtcccc ggacgatatt gaacaatggt tcactgaaga cccaggtcca     180
gatgaagctc ccagaatgcc agaggctgct ccccccgtgg cccctgcacc agcagctcct     240
acaccggcgg cccctgcacc agcccccctcc tggcccctgt catcttctgt cccttcccag     300
aaaacctacc agggcagcta cggtttccgt ctgggcttct tgcattctgg gacagccaag     360
tctgtgactt gcacgtactc ccctgccctc aacaagatgt tttgccaact ggccaagacc     420
tgccctgtgc agctgtgggt tgattccaca ccccgcccg gcacccgcgt ccgcgccatg     480
gccatctaca gcagtcaca gcacatgacg gaggttgtga ggcactgccc ccaccatgag     540
cgctgctcag atagcgatgg tctggcccct cctcagcatc ttatccgagt ggaaggaaat     600
ttgcgtgtgg agtatttgga tgacagaaac acttttcgac atagtgtggt ggtgccctat     660
gagccgcctg aggttggctc tgactgtacc accatccact acaactacat gtgtaacagt     720
tcctgcatgg gcggcatgaa ccggaggccc atcctcacca tcatcacact ggaagactcc     780
agtggtaatc tactgggacg aacagcttt gaggtgcgtg tttgtgcctg tcctgggaga     840
gaccggcgca cagaggaaga gaatctccgc aagaaagggg agcctcacca cgagctgccc     900
ccagggagca ctaagcgagc actgcccaac aacaccagct cctctcccca gccagcggcg     960
gcaccactgg atgagaata tttcacccett cagatccgtg ggcgtgagcg cttcgagatg    1020
ttccgagagc tgaatgaggc cttggaactc aaggatgccc aggctgggaa ggagccaggg    1080
gggagcaggg ctcactccag ccacctgaag tccaaaaagg gtcagtctac ctcccgccat    1140
aaaaaactca tgttcaagac agaagggcct gactcagac                           1179
```

<210> SEQ ID NO 5
<211> LENGTH: 1923
<212> TYPE: DNA
<213> ORGANISM: Artificial sequence
<220> FEATURE:
<223> OTHER INFORMATION: YFP tagged mutant p53 coding sequence

<400> SEQUENCE: 5

```
atggaggagc cgcagtcaga tcctagcgtc gagccccctc tgagtcagga aacattttca      60
gacctatgga aactacttcc tgaaaacaac gttctgtccc ccttgccgtc ccaagcaatg     120
gatgatttga tgctgtcccc ggacgatatt gaacaatggt tcactgaaga cccaggtcca     180
gatgaagctc ccagaatgcc agaggctgct ccccccgtgg cccctgcacc agcagctcct     240
acaccggcgg cccctgcacc agcccccctcc tggcccctgt catcttctgt cccttcccag     300
aaaacctacc agggcagcta cggtttccgt ctgggcttct tgcattctgg gacagccaag     360
tctgtgactt gcacgtactc ccctgccctc aacaagatgt tttgccaact ggccaagacc     420
tgccctgtgc agctgtgggt tgattccaca ccccgcccg gcacccgcgt ccgcgccatg     480
gccatctaca gcagtcaca gcacatgacg gaggttgtga ggcactgccc ccaccatgag     540
```

```
cgctgctcag atagcgatgg tctggcccct cctcagcatc ttatccgagt ggaaggaaat    600
ttgcgtgtgg agtatttgga tgacagaaac acttttcgac atagtgtggt ggtgccctat    660
gagccgcctg aggttggctc tgactgtacc accatccact acaactacat gtgtaacagt    720
tcctgcatgg gcggcatgaa ccggaggccc atcctcacca tcatcacact ggaagactcc    780
agtggtaatc tactgggacg gaacagcttt gaggtgcgtg tttgtgcctg tcctgggaga    840
gaccggcgca cagaggaaga gaatctccgc aagaaagggg agcctcacca cgagctgccc    900
ccagggagca ctaagcgagc actgcccaac aacaccagct cctctcccca gccagcggcg    960
gcaccactgg atgagaata tttcacccctt cagatccgtg ggcgtgagcg cttcgagatg   1020
ttccgagagc tgaatgaggc cttggaactc aaggatgccc aggctgggaa ggagccaggg   1080
gggagcaggg ctcactccag ccacctgaag tccaaaaagg gtcagtctac ctcccgccat   1140
aaaaaactca tgttcaagac agaagggcct gactcagacg cggccgcgga tccttcaggt   1200
actggcagtg tgagcaaggg cgaggagctg ttcaccgggg tggtgcccat cctggtcgag   1260
ctggacggcg acgtaaacgg ccacaagttc agcgtgtccg gcgagggcga gggcgatgcc   1320
acctacggca agctgaccct gaagctgatc tgcaccaccg gcaagctgcc cgtgccctgg   1380
cccaccctcg tgaccaccct gggctacggc ctgcagtgct tcgcccgcta ccccgaccac   1440
atgaagcagc acgacttctt caagtccgcc atgcccgaag gctacgtcca ggagcgcacc   1500
atcttcttca aggacgacgg caactacaag acccgcgccg aggtgaagtt cgagggcgac   1560
accctggtga accgcatcga gctgaagggc atcgacttca aggaggacgg caacatcctg   1620
gggcacaagc tggagtacaa ctacaacagc cacaacgtct atatcaccgc cgacaagcag   1680
aagaacggca tcaaggtgaa cttcaagatc cgccacaaca tcgaggacgg cggcgtgcag   1740
ctcgccgacc actaccagca gaacaccccc atcggcgacg gccccgtgct gctgcccgac   1800
aaccactacc tgagctacca gtccgccctg agcaaagacc ccaacgagaa gcgcgatcac   1860
atggtcctgc tggagttcgt gaccgccgcc gggatcactc tcggcatgga cgagctgtac   1920
aag                                                                 1923
```

<210> SEQ ID NO 6
<211> LENGTH: 641
<212> TYPE: PRT
<213> ORGANISM: Artificial sequence
<220> FEATURE:
<223> OTHER INFORMATION: YFP tagged mutant p53

<400> SEQUENCE: 6

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110
```

-continued

```
Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg His Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Ala Ala
305                 310                 315                 320

Ala Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp Ala Ala Ala Asp Pro Ser Gly
385                 390                 395                 400

Thr Gly Ser Val Ser Lys Gly Glu Glu Leu Phe Thr Gly Val Val Pro
                405                 410                 415

Ile Leu Val Glu Leu Asp Gly Asp Val Asn Gly His Lys Phe Ser Val
            420                 425                 430

Ser Gly Glu Gly Glu Gly Asp Ala Thr Tyr Gly Lys Leu Thr Leu Lys
        435                 440                 445

Leu Ile Cys Thr Thr Gly Lys Leu Pro Val Pro Trp Pro Thr Leu Val
    450                 455                 460

Thr Thr Leu Gly Tyr Gly Leu Gln Cys Phe Ala Arg Tyr Pro Asp His
465                 470                 475                 480

Met Lys Gln His Asp Phe Phe Lys Ser Ala Met Pro Glu Gly Tyr Val
                485                 490                 495

Gln Glu Arg Thr Ile Phe Phe Lys Asp Asp Gly Asn Tyr Lys Thr Arg
            500                 505                 510

Ala Glu Val Lys Phe Glu Gly Asp Thr Leu Val Asn Arg Ile Glu Leu
        515                 520                 525

Lys Gly Ile Asp Phe Lys Glu Asp Gly Asn Ile Leu Gly His Lys Leu
```

```
                530                 535                 540
Glu Tyr Asn Tyr Asn Ser His Asn Val Tyr Ile Thr Ala Asp Lys Gln
545                 550                 555                 560

Lys Asn Gly Ile Lys Val Asn Phe Lys Ile Arg His Asn Ile Glu Asp
                565                 570                 575

Gly Gly Val Gln Leu Ala Asp His Tyr Gln Gln Asn Thr Pro Ile Gly
                580                 585                 590

Asp Gly Pro Val Leu Leu Pro Asp Asn His Tyr Leu Ser Tyr Gln Ser
                595                 600                 605

Ala Leu Ser Lys Asp Pro Asn Glu Lys Arg Asp His Met Val Leu Leu
                610                 615                 620

Glu Phe Val Thr Ala Ala Gly Ile Thr Leu Gly Met Asp Glu Leu Tyr
625                 630                 635                 640

Lys

<210> SEQ ID NO 7
<211> LENGTH: 51
<212> TYPE: PRT
<213> ORGANISM: Artificial sequence
<220> FEATURE:
<223> OTHER INFORMATION: Proteasome Inhibitor Reporter (PIR), Bipartite
      Nuclear Localization Signal

<400> SEQUENCE: 7

Pro Gly Ser Thr Lys Arg Ala Leu Pro Asn Asn Thr Ser Ser Ser Pro
1               5                   10                  15

Gln Pro Ala Ala Ala Pro Leu Asp Gly Glu Tyr Phe Thr Leu Gln Ile
                20                  25                  30

Arg Gly Arg Glu Arg Phe Glu Met Phe Arg Glu Leu Asn Glu Ala Leu
            35                  40                  45

Glu Leu Lys
    50
```

PROTEASOME INHIBITORS AND USES THEREOF

RELATED APPLICATIONS

This application is a division of U.S. patent application Ser. No. 13/322,453 filed on Nov. 24, 2011, which is a National Phase of PCT Patent Application No. PCT/IL2010/000417 filed on May 26, 2010, which claims the benefit of priority from U.S. Provisional Patent Application No. 61/213,299 filed on May 27, 2009. The contents of the above applications are all incorporated herein by reference.

SEQUENCE LISTING STATEMENT

The ASCII file, entitled 56508SequenceListing.txt, created on Apr. 29, 2013, comprising 83,456 bytes, submitted concurrently with the filing of this application is incorporated herein by reference.

FIELD AND BACKGROUND OF THE INVENTION

The present invention, in some embodiments thereof, relates to proteasome inhibitors and uses thereof.

The proteasome is the major proteolytic complex, responsible, in eukaryotic cells, for the degradation of a multitude of cellular proteins. This multi-protein complex, present in both the cytoplasm and the nucleus, catalyzes the ATP-dependent proteolysis of short-lived regulatory proteins, as well as the rapid elimination of damaged and abnormal proteins. The 26S proteasome is a large complex of ~2.5 MDa. Based on biochemical analyses, this complex can be dissociated into two functionally distinct subcomplexes, the 20S core particle (CP) which is the proteolytic component, and the 19S regulatory particle (RP), that is responsible for recognizing, unfolding, and translocating polyubiquitinated substrates into the 20S CP, where they are degraded.

The 20S CP is a 670 kDa barrel-shaped protein complex made up of four stacked, seven-membered rings (4×7 subunits), two outer α rings and two inner β rings ($\alpha_{1-7}\beta_{1-7}$ $\beta_{1-7}\alpha_{1-7}$). The two matching α rings are situated in the outer rims of the barrel, facing the 19S regulatory complex. The proteolytic active sites are located on the two identical β-rings, which are positioned in the center of the 20S complex. In eukaryotes, the catalytic activities of the proteasomes are confined to only three of the β-subunits. Although proteasomes can hydrolyze the amide bonds between most amino acids, proteolytic activities measured using fluorogenic substrates define three distinct (although not conclusive) cleavage preferences [5]: β2 possesses tryptic activity (i.e., cleaving after basic residues); β5 displays chymotryptic activity (i.e., cleaving after hydrophobic residues); and β1 has "caspase-like" or "post-acidic" activity. In all three active β-subunits, proteolytic activity is associated with their N-terminal threonine residue, which acts as a nucleophile in peptide-bond hydrolysis.

The use of proteasome inhibitors as drug candidates emerged from the observation that at specific concentrations, they can induce apoptosis in certain leukemia- and lymphoma-derived cells without similarly affecting their non-transformed counterparts. Further development and clinical trials led to the approval of the modified boronic dipeptide Pyz-Phe-boroLeu, known as Bortezomib as a drug for the treatment of multiple myeloma. Most synthetic proteasome inhibitors are short peptides that mimic protein substrates. Typically, the pharmacophore that reacts with and inhibits the threonine residue in the 20S proteasome's active site is bound to the carboxyl residue of the peptide. Some of the typical synthetic inhibitors are peptide aldehydes, peptide vinyl sulfones, peptide boronates, and peptide epoxyketones. Most notable among the natural, bacterially derived non-peptide inhibitors is claso-lactacystin-β-lactone (Omuralide). Related drugs such as Salinosporamide A (NPI-0052) and Carfilzomib (PR-171) are currently in advanced clinical trials. However, despite the extensive efforts invested in proteasome inhibitor development, there is a growing need for novel inhibitory molecules, due to the emergence of drug-resistant cells and the variable effects of existing inhibitors on different cells.

Most of the current assays for proteasome inhibition are based on cell-free assays, which require purification of 26S or 20S proteasomes from different sources. Such assays may, in principle, be adapted to high-throughput screens, yet they may fail to predict the inhibitory activity in live cells. To overcome this problem, cell-based screens have been incorporated into the drug discovery process. For example, a modified "classical" method for measurement of the chymotrypsin-like, trypsin-like, or caspase-like proteasome activities in cultured cells [Moravec R A et al., 2009, Anal Biochem 387: 294-302] is currently available from Promega Corporation. A number of fluorescent reporter molecules have been also usefully employed to monitor the activity of the proteasome. Dantuma et al constructed a fusion of GFP to Ubiquitin (Ubi[G76V]-GFP) using a standard peptide bond at the N-terminus [Nat Biotechnol 18: 538-543, 2000]. Another proteasome sensor construct, which is a GFP fusion to an artificial peptide, CL1, identified in yeast has been designed by Bence et al (Science 292: 1552-1555, 2001). The Andreatta group and BD Biosciences Clontech has introduced a sensor cell line expressing a GFP fusion protein with a fragment of the mouse ornithine decarboxylase (MODC), which is degraded by the proteasome without the requirement for ubiquitination [Andreatta et al, 2001, Biotechniques 30: 656-660]. An additional reporter cell line, based on the stable expression of a $p27^{kip1}$-GFP fusion was recently employed for the discovery of a novel proteasome inhibitor, argyrin A [Nickeleit I et al., 2008, Cancer Cell 14: 23-35]. The common feature of most of these GFP-fused reporters is that they are based on proteins rapidly degraded by the proteasome under normal conditions, leading to very low fluorescence of the cells, while following inhibition of proteasome activity, the overall fluorescent signal of the cells rapidly increases as a result of accumulation of the reporter proteins.

SUMMARY OF THE INVENTION

According to an aspect of some embodiments of the present invention there is provided a method of treating a disease in which inhibiting of a proteasome is advantageous, the method comprising administering to the subject a therapeutically effective amount of a compound selected from the group consisting of NSC321206, NSC310551, NSC99671 and NSC3907, thereby treating the disease.

According to an aspect of some embodiments of the present invention there is provided a method of treating a disease in which inhibiting of a proteasome is advantageous, the method comprising administering to the subject a therapeutically effective amount of a compound which binds to a proteasome of a cell, the compound comprising a copper bound to a ligand, the ligand being configured such that upon binding to the proteasome, the copper interacts with cysteine 31 of a β2 subunit of the proteasome and further interacts with cysteine 118 of a β3 subunit of the proteasome, thereby treating the disease.

According to an aspect of some embodiments of the present invention there is provided a method of identifying a proteasome inhibitor, the method comprising:

(a) contacting a candidate inhibitor with a population of cells which express the isolated polypeptide of the present invention; and (b) analyzing a cellular location of the polypeptide in the population of cells, wherein a change in localization of the polypeptide is indicative of the candidate inhibitor being a proteasome inhibitor.

According to an aspect of some embodiments of the present invention there is provided an isolated polypeptide comprising a p53 amino acid sequence, having a different cellular location in a presence or absence or a proteasome inhibitor, the polypeptide being linked to a detectable moiety.

According to an aspect of some embodiments of the present invention there is provided a cell population expressing the polypeptide of the present invention.

According to an aspect of some embodiments of the present invention there is provided a pharmaceutical composition comprising as an active ingredient a compound selected from the group consisting of NSC321206, NSC310551, NSC99671 and NSC3907 and a pharmaceutically acceptable carrier.

According to an aspect of some embodiments of the present invention there is provided a pharmaceutical composition comprising as an active ingredient a compound which binds to a proteasome of a cell, the compound comprising a copper bound to a ligand, the ligand being configured such that upon binding to the proteasome, the copper interacts with cysteine 31 of a β2 subunit of the proteasome and further interacts with cysteine 118 of a β3 subunit of the proteasome.

According to an aspect of some embodiments of the present invention there is provided a pharmaceutical composition comprising as an active ingredient a compound identified according to the method of the present invention and a pharmaceutically acceptable carrier.

According to an aspect of some embodiments of the present invention there is provided an isolated polynucleotide comprising a nucleic acid sequence encoding the polypeptide of the present invention.

According to some embodiments of the invention, the disease is cancer.

According to some embodiments of the invention, the disease is an inflammatory disease.

According to some embodiments of the invention, the disease is a neurodegenerative disease.

According to some embodiments of the invention, the isolated polypeptide comprises an amino acid sequence as set forth by SEQ ID NO: 3.

According to some embodiments of the invention, the isolated polypeptide comprises an amino acid sequence as set forth by SEQ ID NO: 6.

According to some embodiments of the invention, the isolated has a nuclear location in a presence of a proteasome inhibitor and a cytoplasmic location in an absence of a proteasome inhibitor.

According to some embodiments of the invention, the isolated polynucleotide comprises a nucleic acid sequence as set forth in SEQ ID NO: 4.

According to some embodiments of the invention, the isolated polynucleotide comprises a nucleic acid sequence as set forth in SEQ ID NO: 5.

According to some embodiments of the invention, the cell population comprises H1299 non-small cell lung carcinoma cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic representation of the PIR protein. PIR protein consists of the yellow fluorescent protein (YFP) fused to the C-terminus of the human mutant (R175H) p53, carrying triple mutation in the bipartite Nuclear Localization Signal (SEQ ID NO: 7) in which three consecutive lysine residues Lys-319, -320, and -321 were replaced with alanines.

FIGS. 2A-I are photographs illustrating nuclear accumulation of the PIR protein upon treatment with proteasome inhibitors. A-H: PIR cells were exposed to MG132, bortezomib and ALLN at the indicated concentrations for 6 hours and monitored for YFP-fluorescence for PIR reporter (upper panel) or stained with anti-beta-catenin antibody (lower panel). I: PIR cells were incubated for 6 h without proteasome inhibitor (control) or with 10 μM MG132. Cell lysates were separated for cytoplasm and nuclear fractions. A band corresponding to the PIR reporter was detected by western blot with a polyclonal anti-p53 antibody.

FIGS. 3A-H are photographs illustrating that murine double minute 2 (MDM2) promotes PIR nuclear translocation. Overexpression of MDM2 results in PIR nuclear localization in the absence of additional stimuli. PIR cells were transfected with wild-type MDM2, MDM2 mutant deficient on p53 binding (D 9-58), or MDM2 mutant with abolished E3 ligase site (Ser 440). Cells expressing both p53 and MDM2 were visualized by immunofluorescence staining with the anti-MDM2 monoclonal antibodies. PIR has a nuclear localization in the cells expressing wt MDM2 and MDM2 (Ser 440), and remains cytoplasmic in the cells transfected with MDM2 (D 9-58).

FIGS. 4A-H are photographs illustrating that Mdm2 siRNA prevents bortezomide-induced translocation of PIR to the nucleus. PIR cells were transiently transfected with 200 pmol control-siRNA or Mdm2-siRNA. Forty-eight hours after transfection, bortezomide (0.1 μM) was added for an additional 6 hours, and immunofluorescence staining for MDM2 was performed as described in Materials and Methods.

Figure 5:
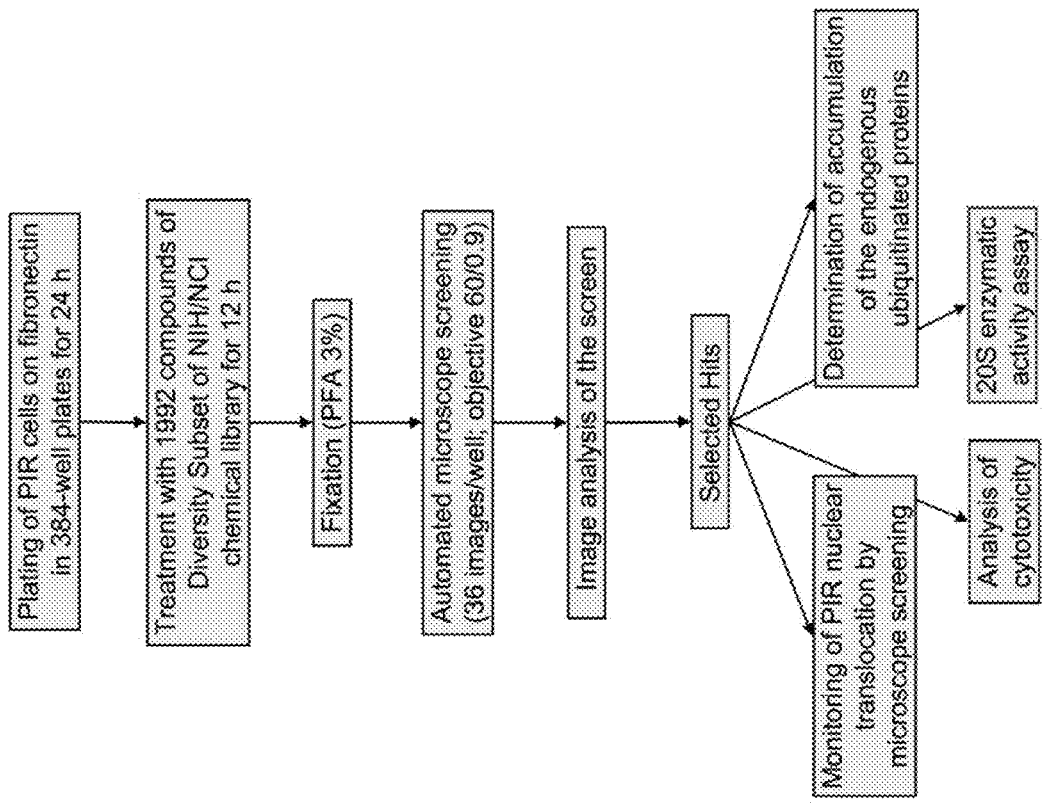

FIG. 5 is a flow chart of the screen procedure. For the screening assay H11299-PIR reporter cells were plated in 384-well plates for 24 hours and treated with compounds of NCI Diversity Set library at two concentrations (1 and 10 µM), using a single compound per well. Following 12 hours of incubation, the cells were fixed by 3% paraformaldehyde and screened for localization of the PIR protein by automated microscope system. Cell images were analyzed for PIR nuclear translocation and selected hits were confirmed by microscopic and biochemical methods, followed by test for compound cytotoxicity.

FIG. 6 is a table illustrating the effect of the candidate inhibitors identified in the screen on PIR cellular localization.

Figures 7A, 7B:
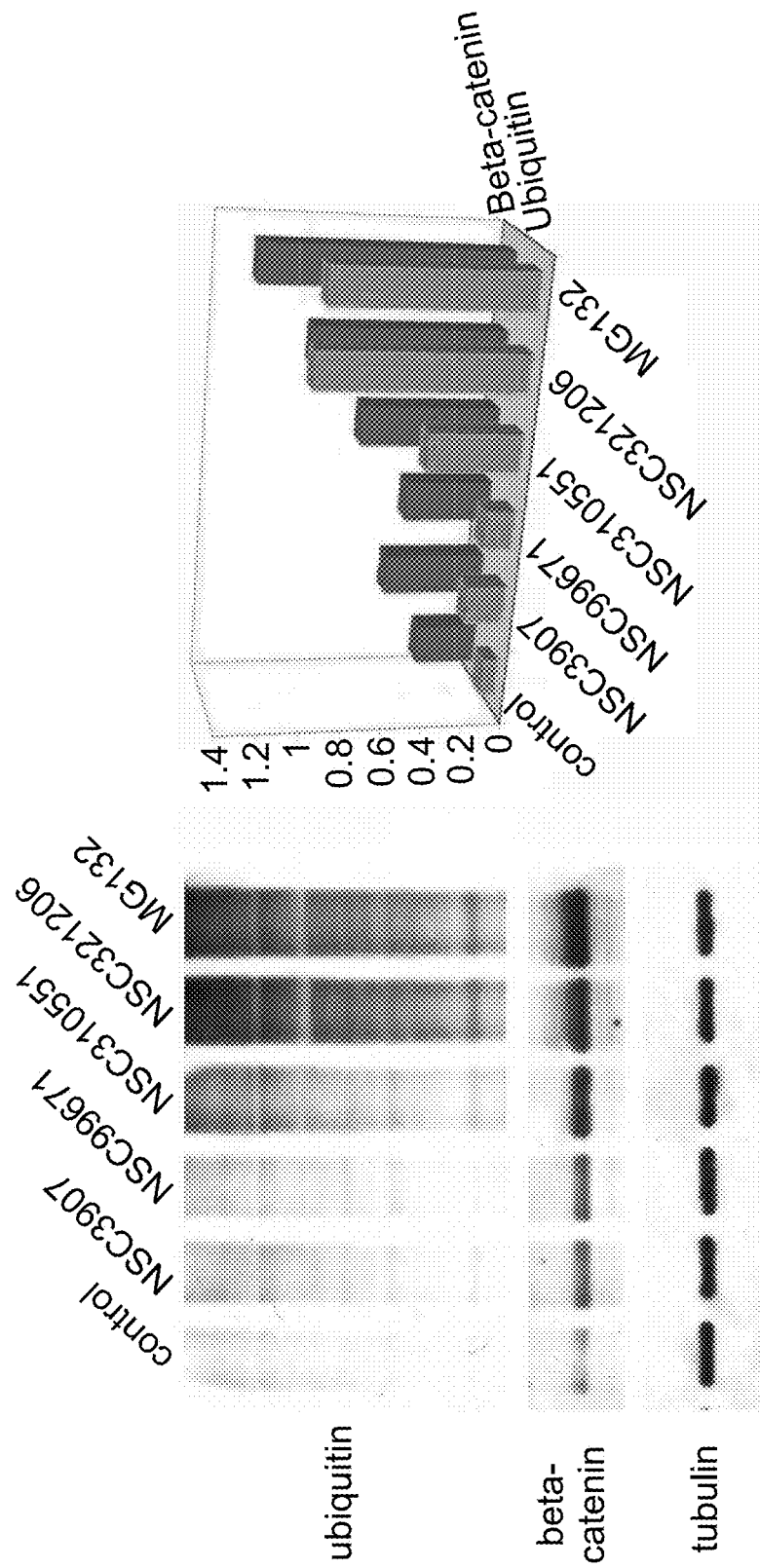

FIGS. 7A-B are photographs and graphs illustrating an increase of ubiquitinated proteins of a whole-cell lysate upon treatment with hit compounds. PIR cells were treated with hit compounds for 6 hours in following concentrations: NSC3907—20 µM, NSC99671—50 µM, NSC310551—0.3 µM, NSC321206—0.15 µM. Known proteasome inhibitor MG132 (5 µM) was used as a positive control. Whole lysates of the PIR cells were immunoblotted for ubiquitin (upper panel) and beta-catenin (middle panel). The tubulin (lower panel) signal represents the internal loading control.

Figure 8:
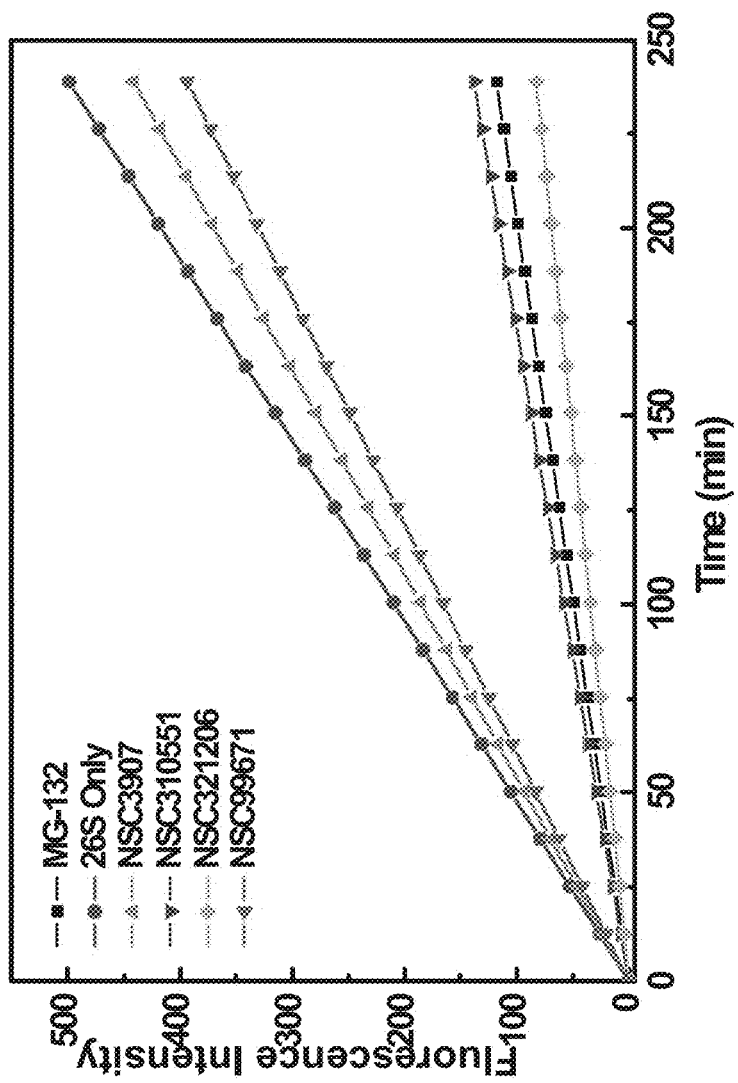

FIG. 8 is a graph illustrating in vitro proteasomal inhibition by the candidate inhibitors. Rabbit muscle purified 26S proteasome was incubated for the indicated time in the presence of 30 µM of the candidate inhibitors (100 µM for NSC3907), MG-132 at 5 µM concentration serves as a control.

Figure 9:
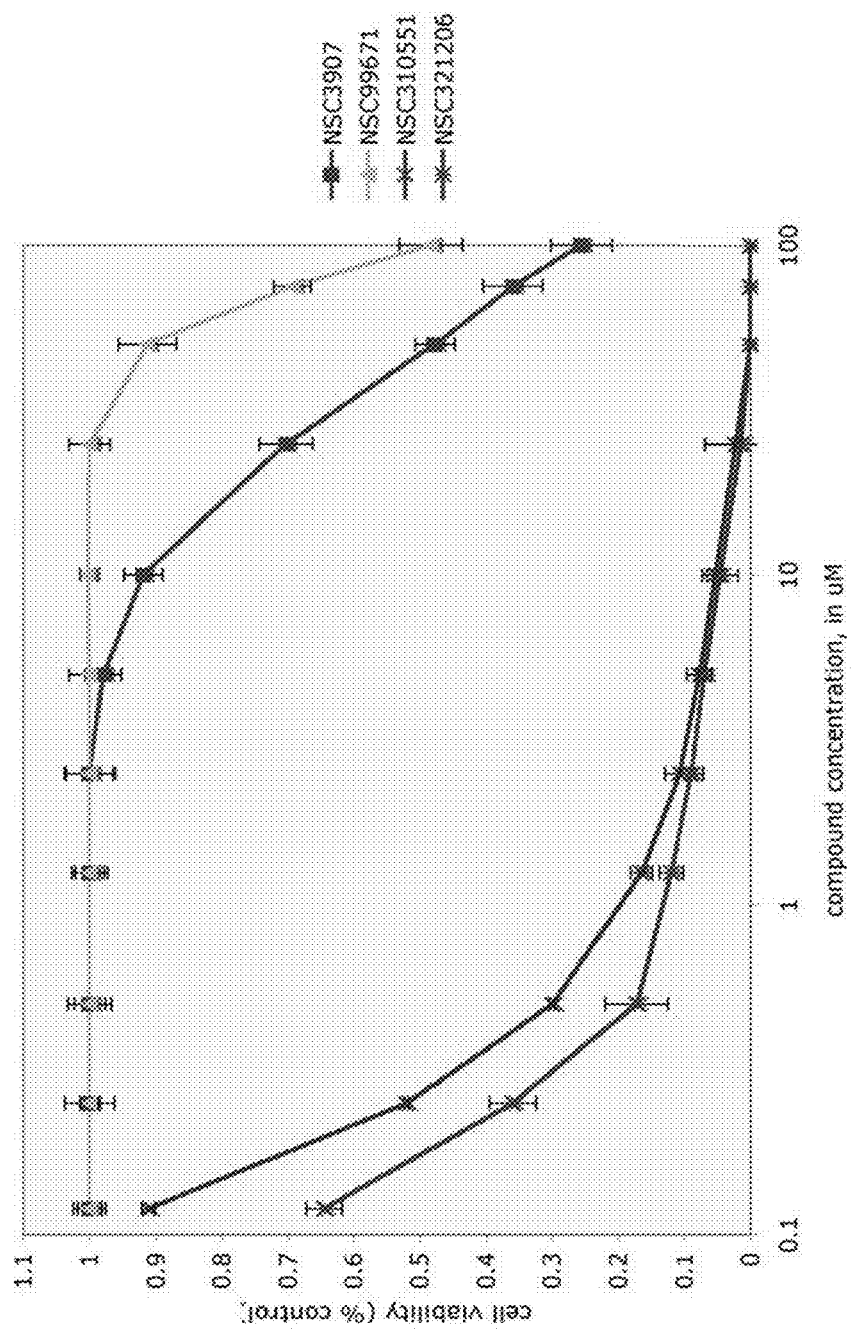

FIG. 9 is a graph illustrating cytotoxic activity of the candidate inhibitors. A: PIR-H1299 cells were treated with hit compounds for 48 hours at 11 concentrations between 0.1 and 100 µM. Cell viability assay was carried out as described (Materials and Methods). Results are expressed as $GI_{50}$, concentration that reduced by 50% the growth of treated cells with respect to untreated controls. All results are displayed as the mean and standard deviation from six replicate wells.

Figure 10:
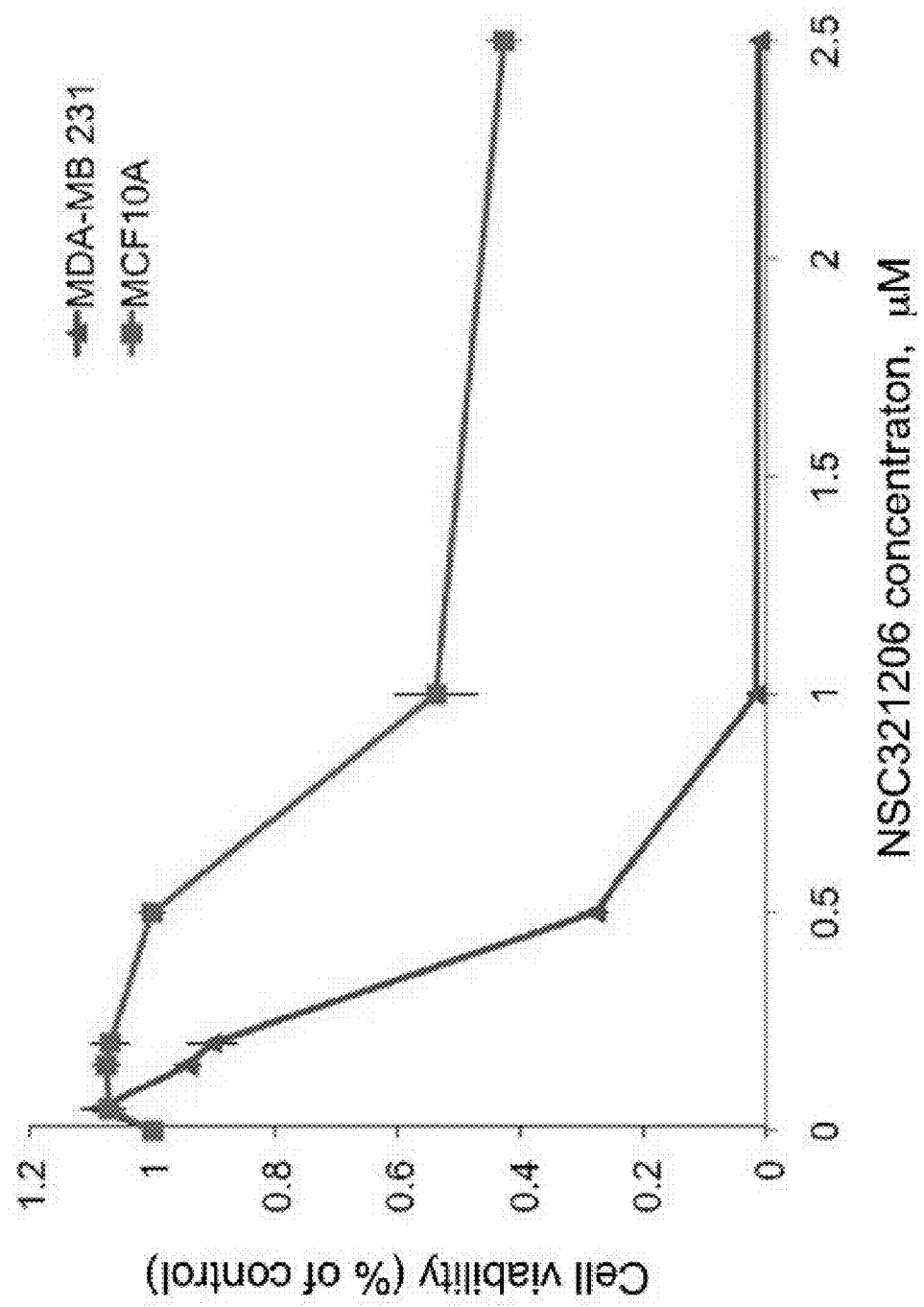

FIG. 10 is a graph illustrating the effect of NSC321206 on cancer cell viability.

Figure 11:
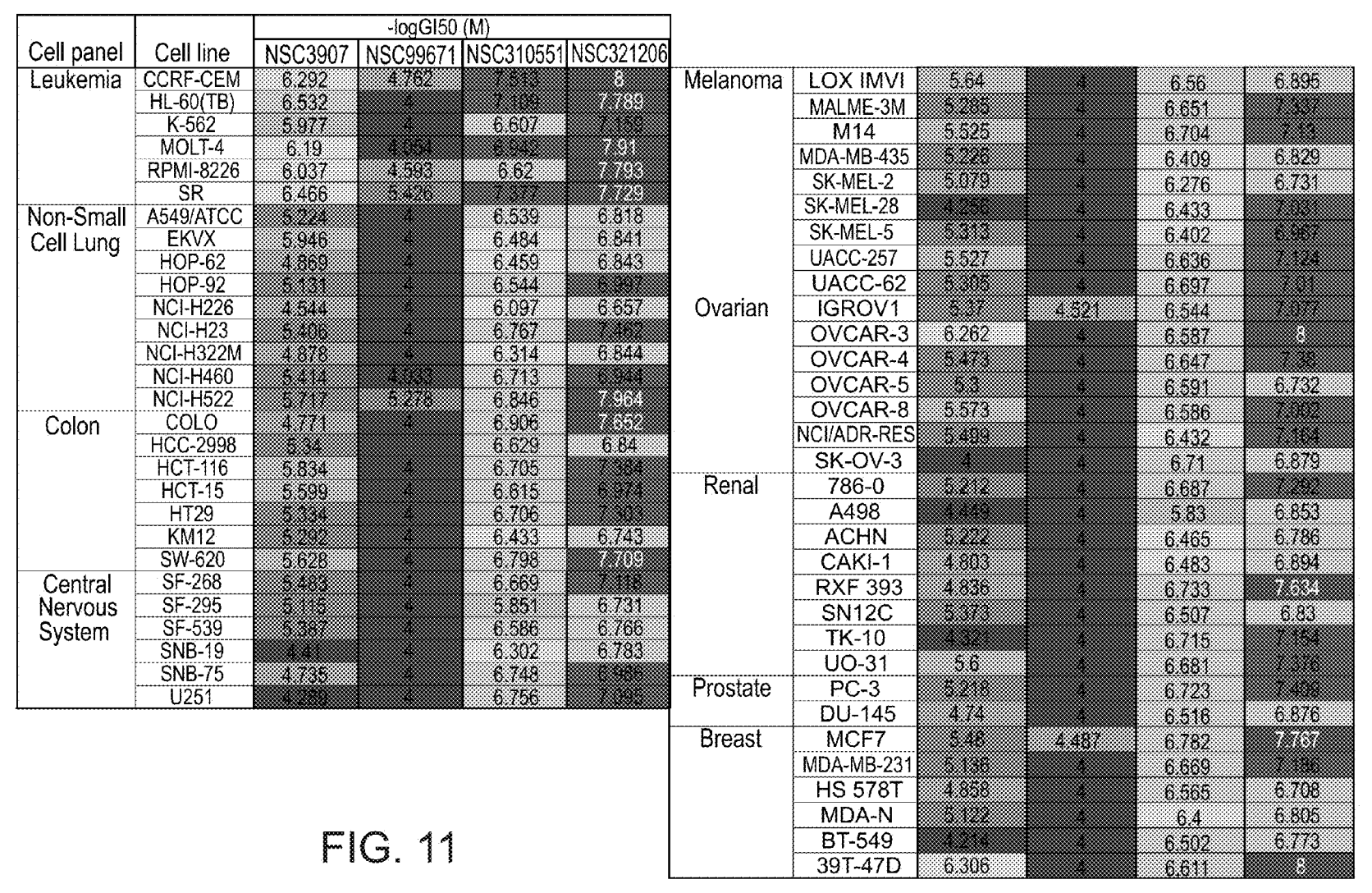

FIG. 11 is a chart presenting the in vitro cytotoxicity of the candidate inhibitors on NCI-60 panel of human tumor cell lines. The results is based on the data from the anticancer drug screening against the full panel of 60 human cancer cell lines conducted as a part of the Developmental Therapeutics Program at the National Cancer Institute. The panel is organized into nine subpanels representing diverse histologies: leukemia, melanoma, and cancers of lung, colon, kidney, ovary, breast, prostate, and central nervous system. The results obtained with this test expressed as the −log of the molar concentration that inhibited the cell growth by 50% (−log $GI_{50}$>4.00 for active compounds).

Figure 12B:
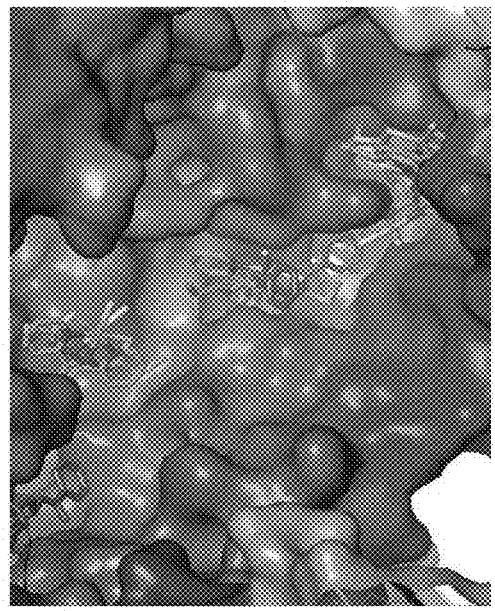
Figure 12A:
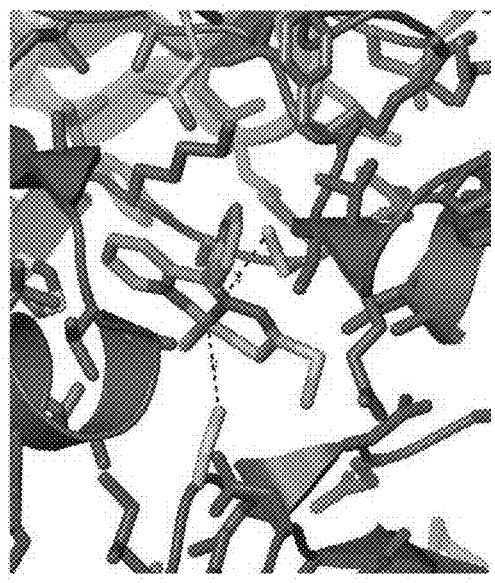

FIGS. 12A-B are illustrations of the potential docking site for NSC321206 pertaining to the Trypsin-like active site. FIG. 12A illustrates the deep hydrophobic pocket in the trypsin-like active site and two Cys residues therein positioned in the ideal conformation with regards to the Cu atom of the NSC321206. FIG. 12B is a space filling cartoon of the Trypsin-like active site. The catalytic threonine is depicted as an orange patch and the Velcade backbone is outlined in red. The three most energetically favored clusters of NSC321206 are presented.

DESCRIPTION OF SPECIFIC EMBODIMENTS OF THE INVENTION

The present invention, in some embodiments thereof, relates to proteasome inhibitors and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Proteasomes are enzymes with a complex structure and function. They are found abundantly in all cells, both normal and cancerous, and are responsible for the degradation of all regulatory proteins. Since regulatory proteins are key to the activation or repression of many cellular processes, including cell-cycle progression, transcription, and apoptosis, the proteasome has become a potential target for inhibition for the treatment of a myriad of disorders.

Using a novel image-based screening approach, the present inventors tested a battery of chemical compounds, and identified four with pronounced proteasome inhibitory activity (FIGS. 7A-B and FIG. 8). The screen was based on the use of H1299 reporter cell line stably expressing a fluorescent Proteasome Inhibition Reporter (PIR) protein. The rational of the screen builds on the finding that upon inhibition of proteasomal activity this reporter translocates to the nucleus, resulting in a distinct and detectable nuclear fluorescent signal. The findings demonstrate that this approach is highly sensitive and compatible with high-throughput microscopy.

The present inventors further showed that at least one of these inhibitors (NSC321206) could selectively kill cancerous cells as opposed to non-cancerous cells (FIG. 10).

Computer analysis of the 3D structure of the proteasome and the NSC321206 inhibitor, served to identify putative docking sites on the proteasome for the inhibitor. The present inventors postulate that the identified sites may be used to design additional small molecules based on NSC321206 that would strongly interact with these binding sites and thus would inhibit proteasomal activity.

As is described in the Examples section that follows, it was deduced from these studies that the proteasome comprise two cysteines in, or close to, the trypsin-like active site of the proteasome, which interact with a copper of the NSC321206 inhibitor (FIGS. 12A-B). It was thus deduced that in order to achieve a maximized number and strength of interactions with these binding sites, small molecules may be designed such that they comprise a copper in a suitable proximity and orientation to these binding sites.

Thus, according to one aspect of the present invention there is provided an isolated polypeptide comprising a p53 amino acid sequence, having a different cellular location in a presence or absence or a proteasome inhibitor, the polypeptide being linked to a detectable moiety.

The term "p53" refers to the human p53 polypeptide that has at least 70%, at least 80%, at least 90% or at least 95% sequence homology to SEQ ID NO: 1.

The present inventors contemplate all p53 sequences having a cellular location which is influenced by the presence of a proteasome inhibitor e.g., soluble (i.e. cytoplasmic) or membrane bound, a specific cellular organelle, or a specific biochemical pathway, e.g., replication, transcription or translation, etc. Exemplary cellular organelles include nuclei, mitochondrion, chloroplast, ribosome, ER, Golgi apparatus, lysosome, proteasome, secretory vesicle, vacuole and microsome.

The present inventors have shown that a mutation in the nuclear localization signal of the p53 polypeptide serves to alter the native nuclear localization of the polypeptide to a cytoplasmic location. However, in the presence of a proteasome inhibitor, the p53 polypeptide reverts to its nuclear location.

Thus, according to one embodiment, the p53 polypeptide has a cytoplasmic location in an absence of a proteasome inhibitor and a nuclear location in a presence of a proteasome inhibitor.

With reference to a particular location, the present invention contemplates that at least 70%, more preferably at least 75%, more preferably at least 80%, more preferably at least 85%, at least 90% and even more preferably at least 95% of the polypeptide is situated at that particular location, wherein the remaining polypeptide is situated at any other location in the cell.

Contemplated mutations include for example a mutation at a position corresponding to lysine 319 of SEQ ID NO: 1, a mutation at a position corresponding to lysine at 320 of SEQ ID NO: 1 and a mutation at a position corresponding to lysine 321 of SEQ ID NO: 1.

As used herein, the term "mutation" refers to an alteration in an amino acid sequence compared to the wild type sequence (GenBank Accession No: NP_000537.3—SEQ ID NO: 1)

The mutation may comprise a deletion or a substitution. Exemplary mutations include at least one of an alanine corresponding to lysine at position 319, an alanine corresponding to lysine at position 320 and an alanine corresponding to lysine at position 321.

Thus, for example the present inventors contemplate the use of a polypeptide having an amino acid sequence as set forth in SEQ ID NO: 2.

The p53 polypeptide may further comprise mutations which act to increase the half-life thereof.

Accordingly, the present inventors contemplate the use of a p53 polypeptide having a mutation of an arginine corresponding to histidine at position 175.

Thus, for example the present inventors contemplate the use of a polypeptide having an amino acid sequence as set forth in SEQ ID NO: 3.

Other mutations that may serve to increase the half life of the p53 include those described in Joerger A C, Fersht A R. Structural biology of the tumor suppressor p53 and cancer-associated mutants. Adv Cancer Res. 2007; 97:1-23), incorporated herein by reference.

In addition, the p53 polypeptide of the present invention may comprise other conservative variations of SEQ ID NO: 1.

The phrase "conservative variation" as used herein refers to the replacement of an amino acid residue by another, biologically similar residue. Examples of conservative variations include the substitution of one hydrophobic residue such as isoleucine, valine, leucine, or methionine for another, or the substitution of one solar residue for another, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Other mutations which impart stability or alter the cellular localization of p53 to a cytoplasmic one can be uncovered using computational biology. For example, various mutated P53 peptide sequences can be computationally analyzed for an ability to impart stability and cellular localization using a variety of three dimensional computational tools. Software programs useful for displaying three-dimensional structural models, such as RIBBONS (Carson, M., 1997. Methods in Enzymology 277, 25), O (Jones, T A. et al., 1991. Acta Crystallogr. A47, 110), DINO (DINO: Visualizing Structural Biology (2001) www.dino3d.org); and QUANTA, INSIGHT, SYBYL, MACROMODE, ICM, MOLMOL, RASMOL and GRASP (reviewed in Kraulis, J., 1991. Appl Crystallogr. 24, 946) can be utilized to model prospective mutant peptide sequences to identify useful mutations.

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Table 1 below lists naturally occurring amino acids which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

As mentioned, the p53 polypeptide of this aspect of the present invention is linked to a detectable moiety. An exemplary p53 polypeptide linked to a detectable moiety has an amino acid sequence as set forth in SEQ ID NO: 6.

The detectable moiety can be any one which is capable of producing, either directly or indirectly, a detectable signal. For example, the detectable moiety may be a radioisotope, a fluorescent or chemiluminescent compound, or a tag (to which a labeled antibody can bind).

Examples of suitable fluorescent detectable moieties include, but are not limited to, phycoerythrin (PE), fluorescein isothiocyanate (FITC), Cy-chrome, rhodamine, Texas red, PE-Cy5, green fluorescent protein, the yellow fluorescent protein, the cyan fluorescent protein and the red fluorescent protein as well as their enhanced derivatives.

Table 2 below provides examples of sequences of identifiable moieties.

TABLE 2

| TIdentifiable Moiety | Amino Acid sequence (Genebank Accession No.) | Nucleic Acid sequence (Genebank Accession No.) |
|---|---|---|
| Green Fluorescent protein | AAL33912 | AF435427 |
| Alkaline phosphatase | AAK73766 | AY042185 |
| Peroxidase | NP_568674 | NM_124071 |
| Histidine tag | AAK09208 | AF329457 |
| Myc tag | AF329457 | AF329457 |
| Biotin lygase tag | NP_561589 | NC_003366 |

TABLE 2-continued

| TIdentifiable Moiety | Amino Acid sequence (Genebank Accession No.) | Nucleic Acid sequence (Genebank Accession No.) |
|---|---|---|
| orange fluorescent protein | AAL33917 | AF435432 |
| Beta galactosidase | NM_125776 | NM_125776 |
| Fluorescein isothiocyanate | AAF22695 | AF098239 |
| Streptavidin | S11540 | S11540 |

For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.].

In order to express the polypeptides of the present invention in cell populations, the encoding DNA sequence is inserted into nucleic acid constructs and cells are transfected using methods commonly known in the art as described further herein below.

Thus, according to another aspect of the present invention there is provided an isolated polynucleotide comprising a nucleic acid sequence encoding a polypeptide which comprises a p53 amino acid sequence, the polypeptide having a different cellular location in a presence or absence or a proteasome inhibitor, the polypeptide being linked to a detectable moiety.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exon sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Exemplary polynucleotides of the present invention comprise the sequences as set forth in SEQ ID NOs: 4 and 5.

As mentioned, the polynucleotides of this aspect of the present invention are typically inserted into nucleic acid constructs suitable for mammalian cell expression.

Such a nucleic acid construct typically includes a promoter sequence for directing transcription of the polynucleotide sequence in the cell in a constitutive or inducible manner.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter (Zabala M, et al., Cancer Res. 2004, 64(8): 2799-804).

The nucleic acid construct may include additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of the present invention is active in the specific cell population transformed.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase RNA stability [Soreq et al., 1974; J. Mol. Biol. 88: 233-45).

Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Nucleic acid constructs containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

According to one embodiment, the nucleic acid construct is a viral vector, such as adenovirus, lentivirus, Herpes simplex I virus, or adeno-associated virus (AAV) and lipid-based systems.

As mentioned herein above, the present inventors have found that cells expressing the polypeptide of this aspect of the present invention can be used as a system for identifying proteasome inhibitors.

Various methods can be used to introduce the expression vector of the present invention into cell populations. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. Useful lipids for lipid-mediated transfer of the gene are, for example, DOTMA, DOPE, and DC-Chol [Tonkinson et al., Cancer Investigation 14(1): 54-65 (1996)].

Contemplated cell populations that may be used for identifying proteasome inhibitors include immortalized cell populations (i.e. cell lines) or cells taken directly from a living organism. According to one embodiment, the cell populations are homogeneous (i.e. comprise only one cell type). According to another embodiment the cells express MDM2 (E3 ubiquitin-protein ligase Mdm2; NC_000012.11). According to one embodiment, the cell population comprises H1299 non-small cell lung carcinoma cells. Other exemplary cell populations include, but are not limited to MCF7 cells, MCF10a (human breast cells), human foreskin fibroblasts and U2OS (human osteosarcoma) cells.

Thus, according to another aspect of the present invention there is provided a method of identifying a proteasome inhibitor, the method comprising:

(a) contacting a candidate inhibitor with a population of cells which express an isolated polypeptide comprising a p53 amino acid sequence, having a different cellular location in a presence or absence or a proteasome inhibitor when expressed in a cell, the polypeptide being linked to a detectable moiety; and (b) analyzing a cellular location of the polypeptide in the population of cells, wherein a change in a localization of the polypeptide is indicative of the candidate inhibitor being a proteasome inhibitor.

The term "proteasome" as used herein refers to the multiprotein complex responsible, in eukaryotic cells, for the degradation of cellular proteins.

The 26S proteasome can be dissociated into two functionally distinct subcomplexes, the 20S core particle (CP) which is the proteolytic component, and the 19S regulatory particle (RP), that is responsible for recognizing, unfolding, and translocating polyubiquitinated substrates into the 20S CP, where they are degraded.

The 20S CP is a 670 kDa barrel-shaped protein complex made up of four stacked, seven-membered rings (4×7 subunits), two outer α rings and two inner β rings ($\alpha_{1-7}\beta_{1-7}\beta_{1-7}\alpha_{1-7}$). The two matching α rings are situated in the outer rims of the barrel, facing the 19S regulatory complex. The proteolytic active sites are located on the two identical β-rings, which are positioned in the center of the 20S complex.

As used herein, the phrase "proteasome inhibitor" refers to a substance (e.g. compound) that inhibits at least one enzymatic activity of the proteasome. Exemplary enzymatic activities of the proteasome include tryptic activity (i.e., cleaving after basic residues) present in the β2 subunit; chymotryptic activity (i.e., cleaving after hydrophobic residues) present in the β5 subunit; and "caspase-like" or "post-acidic" activity present in the β1 subunit.

The phrase "change in location" refers to a change in the cellular distribution of the polypeptide such that at least 70%, at least 80%, at least 90% of the polypeptide is translocated from a first location in the cell (e.g. cytoplasm) to a second location in the cell (e.g. nucleus).

Since the polypeptides of the present invention comprise detectable moieties, analyzing their location in the cell may be performed by various techniques including for example fluorescent microscopy, immunohistochemistry, Western blot analysis (by generating nuclear and cytoplasmic extracts of the cells).

The candidate inhibitors of this aspect of the present invention that may be tested as potential proteasome inhibitors according to the method of the present invention include, but are not limited to, nucleic acids, e.g., polynucleotides, ribozymes, siRNA and antisense molecules (including without limitation RNA, DNA, RNA/DNA hybrids, peptide nucleic acids, and polynucleotide analogs having altered backbone and/or bass structures or other chemical modifications); proteins, polypeptides (e.g. peptides), carbohydrates, lipids and "small molecule" drug candidates. "Small molecules" can be, for example, naturally occurring compounds (e.g., compounds derived from plant extracts, microbial broths, and the like) or synthetic organic or organometallic compounds having molecular weights of less than about 10,000 daltons, preferably less than about 5,000 daltons, and most preferably less than about 1,500 daltons.

Using the above screen, the present inventors tested 1,992 low molecular weight compounds comprising the NCI Diversity Set chemical library and identified four compounds NSC321206, NSC310551, NSC99671 and NSC3907 that were positive in the assay and therefore may be considered as proteasome inhibitors.

As mentioned herein above, the present inventors computer-analyzed the 3D structure of the proteasome and the NSC321206 inhibitor, identifying putative docking sites on the proteasome for the inhibitor. It was deduced from these studies that the proteasome comprise two cysteines in, or close to, the trypsin-like active site of the proteasome, which interact with a copper atom of the NSC321206 inhibitor (FIGS. 12A-B of the Examples section herein below). It was thus deduced that in order to achieve a maximized number and strength of interactions with these binding sites, small molecules may be designed such that they comprise a metal ion in a suitable proximity and orientation to these binding sites.

Thus, according to another aspect of the present invention there is provided a method of treating a disease in which inhibiting of a proteasome is advantageous, the method comprising administering to the subject a therapeutically effective amount of a compound which binds to a proteasome of a cell, the compound comprising copper bound to a ligand, the ligand being configured such that upon binding to the proteasome, the copper interacts with cysteine 31 of a β2 subunit of the proteasome and further interacts with cysteine 118 of a β3 subunit of the proteasome.

The copper can be either a copper atom (having a 0 oxidation state), or a copper ion (having I or II oxidation state).

In cases where the copper is a copper ion, it is bound to one or two anions such as, for example, halides (e.g., bromides).

In some embodiments, the copper is a copper ion. In some embodiments, the copper ion is $Cu^{+1}$. In some embodiments, the copper ion is bound to a bromide.

As used herein the term "ligand" describes a chemical moiety, ion or atom that is associated with a central metal atom, via covalent bonds, ionic bonds and/or coordinative bonds. The ligand can be associated with copper atom or a copper ion.

According to embodiments of the invention, the ligand is selected such that it includes one or more chemical groups that interact with one or more amino acids in the trypsin-like active site of the proteasome, whereby this interaction results in a configuration of the ligand within this active site in which the copper is present in a proximity and orientation of the above-indicated cysteine residues that allows its interaction with these cysteine residues.

In some embodiments, the ligand includes one or more electron donating atoms for forming a complex with the electron-poor copper atom or ion. Suitable electron donating atoms include, but are not limited to, nitrogen, sulfur, and oxygen.

In some embodiments, the ligand includes at least two nitrogen atoms that form coordinative bonds with the copper. Optionally, the ligand includes one or more nitrogen atoms and one or more sulfur atoms.

In some embodiments, the ligand is such that the electron donating atoms (e.g., nitrogen and/or sulfur atoms) form stable 5-membered or 6-membered ring(s) upon coordinatively binding the copper.

In some embodiments, the nitrogen and/or sulfur atoms in the ligand are such that upon coordinatively binding the copper, a rigid structure is formed.

By "rigid structure" it is meant that the number of free-to-rotate bonds in the compound is minimal, namely, is no more than 1 or 2.

The rigid structure assures that the ligand is configured in the active site as desired (as indicated supra) selectively, such that is cannot be subjected to changes in its three-dimensional configuration that could reduce the interaction of the copper with the above-indicated cysteine residues in the active site.

Thus, in some embodiments, the ligand includes electron donating atoms as described herein, which form, upon coordinating the copper, a complex that comprises fused rings.

In some embodiments, the ligand includes electron donating atoms which form with copper a complex that comprises 2 fused rings, optionally and preferably 3 fused rings, and further optionally 4 and even 5 fused rings.

By "fused ring" it is meant that the two or more rings that have two adjacent atoms and the bond therebetween in common.

Each ring in the part of the ligand that is directly associated with the copper can independently be heteroalicyclic or heteroaromatic ring.

In some embodiments, one or more rings, and optionally each ring in this part of the ligand is a heteroaromatic ring. Heteroaromatic rings form a more rigid structure as compared to heteroalicyclic rings.

Exemplary ligands that are suitable for a compound as described herein include, but are not limited to, ligands having a core structure represented by the following general Formula:

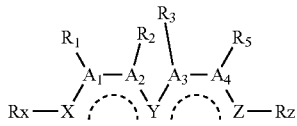

wherein:

the dashed line denotes a saturated or unsaturated bond;

X, Y and Z are each independently an electron donating atom as described herein, preferably selected from the group consisting of nitrogen and sulfur;

$A_1$-$A_4$ are each independently carbon or a heteroatom (e.g., nitrogen, sulfur or oxygen); and Rx, Rz and $R_1$-$R_4$ are each independently hydrogen, alkyl, cycloalkyl, heteroalicyclic, aryl, heteroaryl, alkoxy, thioalkoxy, hydroxy, thiol, amine, amide, sulfonamide, carboxy, thiocarboxy, carbamate, thiocarbamate, or absent, or, alternatively, two or more of Rx, Rz and $R_1$-$R_4$ form a 5- or 6-membered cyclic or heterocyclic ring.

Accordingly, a compound according to these embodiments of the invention has a formula:

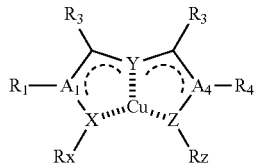

wherein the broken line denotes a coordinative bond; and "Cu" represents either Cu(0) or Cu(I) bound to an anion (e.g., bromide).

It will be appreciated by one of skills in the art that the nature of each of the variables (X, Y, Z, $A_1$-$A_4$, Rx, Rz, and $R_1$-$R_4$) depends on the valency and chemical compatibility of the variable and its position with respect to adjacent variables. Hence, the present invention is aimed at encompassing all the feasible options for any variable.

In some embodiments, the chemical groups flanking the part of the ligand that is directly associated with the copper (e.g., Rx, Rz and $R_1$-$R_4$) are selected so as to interact with amino acids in the above-indicated active site in such a way that results in the desired configuration in which the copper is in a proximity and orientation suitable for binding the above-indicated cysteine residues.

These groups can therefore include, for example, aromatic groups for interacting with aromatic groups in corresponding amino acid residues in the active sites (e.g., phenylalanine, tyrosine, or tryptophan (e.g. the tryptophan may interact with a flanking pyridine), also please indicate other optional interactions); heteroatoms for forming hydrogen bonds with corresponding groups of amino acid residues in the active sites (e.g., lysine, threonine, methionine, serine, asparagine or glutamine).

In some embodiments, one or more of Rx, Rz and $R_1$-$R_4$ comprises an aryl or heteroaryl. In an exemplary embodiment, $R_2$ is an aryl or heteroaryl.

In some embodiments, one or more of Rx, Rz and $R_1$-$R_4$ is alkoxy or thioalkoxy. In an exemplary embodiment, $R_4$ is alkoxy or thioalkoxy.

In some embodiments, two or more of Rx, Rz and $R_1$-$R_4$ form together a cyclic ring, so as to form a compound that comprises at least 3 fused rings.

In some embodiments, Rz and $R_1$ form a heterocyclic ring. In some embodiments, the heterocyclic ring is a heteroaryl. In some embodiments, X is nitrogen and the heteroaryl is pyridine.

In some embodiments, X and Y are each nitrogen and Z is sulfur. Alternatively, X and Z are each sulfur and Y is nitrogen. Further alternatively, each of X, Y and X is nitrogen. Other combinations are also contemplated.

In some embodiments, at least one of the bonds denoted by a dashed line in the formulae hereinabove is an unsaturated bond. In some embodiments, X, Y, Z, $A_1$-$A_4$ and the bonds therebetween are selected so as to form an aromatic system when complexed with copper.

In some embodiments, $A_1$, $A_2$ and $A_4$ are each carbon and $A_3$ is a heteroatom (e.g., nitrogen).

In each of the above-described embodiments, the heteroatom can be neutral, positively charged or negatively charged.

In some embodiments, the compound comprises two or more ligands as described herein, which are coordinating with the copper.

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. Representative examples are pyridine, pyrrole, oxazole, indole, purine and the like.

The term "hydroxyl" describes a —OH group.

The term "alkoxy" describes both an —O-alkyl and an —O-cycloalkyl group, as defined herein.

The term "thiohydroxy" or "thiol" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "carboxylate" encompasses "C-carboxylate", which describes a —C(=O)—OR' group, where R' is as defined herein; and "O-carboxylate", which describes a —OC(=O)R' group, where R' is as defined herein.

The term "thiocarboxylate" encompasses "C-thiocarboxylate", which describes a —C(=S)—OR' group, where R' is as defined herein; and "O-thiocarboxylate", which describes a —OC(=S)R' group, where R' is as defined herein.

The term "carbamate" encompasses "N-carbamate", which describes an R"OC(=O)—NR'— group, with R' and R" as defined herein; and "O-carbamate", which describes an —OC(=O)—NR'R" group, with R' and R" as defined herein.

The term "thiocarbamate" encompasses "O-thiocarbamate", which describes a —OC(=S)—NR'R" group, with R' and R" as defined herein; "N-thiocarbamate", which describes an R"OC(=S)NR'— group, with R' and R" as defined herein; "S-dithiocarbamate", which describes a —SC(=S)—NR'R" group, with R' and R" as defined herein; and "N-dithiocarbamate", which describes an R"SC(=S)NR'— group, with R' and R" as defined herein.

The term "amide" encompasses "C-amide", which describes a —C(=O)—NR'R" group, where R' and R" are as defined herein; and "N-amide", which describes a R'C(=O)—NR"— group, where R' and R" are as defined herein.

The term "S-sulfonamide" describes a —S(=O)$_2$—NR'R" group, with R' as defined herein and R" is as defined herein for R'.

The term "N-sulfonamide" describes an R'S(=O)$_2$—NR"— group, where R' and R" are as defined herein.

Exemplary compounds include NSC321206 and NSC310551, as described herein.

Thus, according to another aspect of the present invention there is provided a method of treating a disease in which inhibiting of a proteasome is advantageous, the method comprising administering to the subject a therapeutically effective amount of a compound selected from the group consisting of NSC321206, NSC310551, NSC99671 and NSC3907, thereby treating the disease.

Because unregulated, proteasome-mediated degradation of vital cell cycle regulatory proteins is an essential component of tumor development, a possible way of arresting or limiting tumor development is by inhibition of the proteasome. Proteasome inhibition leads to the stabilization of these substrates, and, as a result, cell-cycle arrest occurs and the cells ultimately undergo apoptosis. Transformed cells seem to be particularly sensitive to any disturbances of the cell cycle and/or the coordinated production and degradation of all proteins involved in this process, including proteasome inhibitor-induced growth retardation. Consequently, proteasome inhibitors are being actively explored for the treatment of a variety of hematologic malignant neoplasms and solid tumors.

Thus, according to one embodiment, the disease in which inhibiting a proteasome is advantageous is cancer.

Examples of cancers that may be treated using the proteaseome inhibitors of this aspect of the present invention include, but are not limited to adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, malignant melanoma, meningioma; multiple endocrine neoplasia; multiple myeloma, myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, basal cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

According to a specific embodiment, the cancer is multiple myeloma.

The formation of new blood vessels, angiogenesis, is critical for the progression of many diseases, including cancer metastases, diabetic retinopathy, and rheumatoid arthritis. Many factors associated with angiogenesis, eg, cell adhesion molecules, cytokines, and growth factors, are regulated through the proteasome, and, hence, alteration of its activity will affect the degree of vessel formation. Oikawa et al [Biochem Biophys Res Commun. 1998; 246:243-248] demonstrated that a particular proteasome inhibitor, lactacystin significantly reduced angiogenesis, suggesting that it, or related compounds, could be beneficial in disease states that rely on the formation of new blood vessels.

Thus, according to another embodiment, the disease in which inhibiting a proteasome is advantageous is an angiogenesis associated disease.

The proteasome is intimately linked to the production of the majority of the class I antigens. It is therefore conceivable that excessive inhibition of the proteasome might also increase the chance of viral infections such as HIV.

Through its regulation of NF-kappa B, the proteasome is central to the processing of many pro-inflammatory signals. Once released from its inhibitory complex through proteasome degradation of I kappa B, NF-kappa B induces the activation of numerous cytokines and cell adhesion molecules that orchestrate the inflammatory response. Thus, the present invention contemplates use of the proteasome inhibitors of the present invention for the treatment of inflammatory diseases including but not limited to asthma, ischemia and reperfusion injury, multiple sclerosis, rheumatoid arthritis, psoriasis, autoimmune thyroid disease, cachexia, Crohn disease, hepatitis B, inflammatory bowel disease, sepsis, systemic lupus erythematosus, transplantation rejection and related immunology and autoimmune encephalomyelitis.

In addition, it has been shown that blocking proteasome activity reduces neuron and astrocyte degeneration and neutrophil infiltration and therefore can be potential therapy for stroke and neurodegenerative diseases including Parkinson's disease, Alzheimer disease, and amyotrophic lateral sclerosis (ALS).

The proteaseome inhibitors of this aspect of the present invention may be provided per se or as part of a pharmaceutical composition, where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the proteasome inhibitors accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount.

Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (proteasome inhibitor) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to ensure blood or tissue levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Discovery of Novel Proteasome Inhibitors Using a High-Content Cell-Based Screening System Materials and Methods DNA Constructs, Generation of a Stable Reporter Cell Line and Transient Transfection:

To construct a YFP-tagged Proteasome Inhibitor Reporter (PIR) protein, cDNA encoding a full-length human p53 R175H mutant was amplified by PCR from a cDNA clone, and three consecutive lysine residues in the bipartite Nuclear Localization Signal (NLS) were replaced with alanines by PCR-based, site-directed mutagenesis [Higuchi R, et al., (1988) Nucleic Acids Res 16: 7351-7367; Ho S N, et al (1989) Gene 77: 51-59]. The DNA fragment was cloned into the BglII and NotI sites of pLPCX retroviral vector (Clontech) in-frame to the N-terminus of the yellow fluorescent protein (YFP), using the NotI/ClaI restriction sites. The PIR protein was expressed in an H1299 non-small cell lung carcinoma cell line, following retroviral infection, and the cells were cultured in RPMI 1640 medium containing 10% fetal bovine serum, 2 mM glutamine and 1% penicillin-streptomycin (all from Sigma-Aldrich) in a humidified atmosphere of 5% $CO_2$ at 37° C. Fluorescent cells were isolated by flow cytometry, and single-cell cloning was used to generate a morphologically uniform cell population.

Transfections employing plasmid DNA were carried out using Lipofectamine 2000™ reagent (Invitrogen) as per the manufacturer's instructions. For RNA interference, PIR cells were transfected with 50 pM control or MDM2 siRNA oligonucleotides (Dharmacon, ON-TARGETplus SMARTpool), with Dharmafect 2 (Dharmacon) according to the manufacturer's protocol Immunofluorescence Microscopy:

Cells were cultured on glass coverslips, fixed, and permeabilized for 2 minutes in phosphate-buffered saline (PBS) containing 0.5% Triton X-100 and 3% formaldehyde, and post-fixed with 3% formaldehyde in PBS for 30 minutes. The cells were then rinsed and stained with polyclonal anti-β-catenin antibody (Sigma) or a mixture of anti-MDM2 monoclonal antibodies SMP14, 2A10, and 4B11 for 1 hour, washed, and further incubated with Cy3-conjugated goat anti-mouse IgG (Enco). Images were acquired using the DeltaVision system (Applied Precision Inc.).

Compound Library:

The chemical compound library screened for proteasomal inhibitors consisted of the NCI Diversity Set, containing 1,992 low molecular weight synthetic compounds selected from and representing nearly 140,000 compounds available from the NCI DTP chemical library (www.dtp.nci.nih.gov/branches/dscb/diversity explanation.html).

The library compounds were dissolved in dimethyl sulfoxide (DMSO) to a concentration of 10 mM, placed in 96-well plates, and stored at −70° C. for future use.

Image-Based Screening Assay for Proteasome Activity:

PIR-expressing H1299 cells were seeded at a density of 800 cells per well in 384-well assay plates (F-bottom, μClear, black, tissue-culture-treated) (Greiner Bio-One). Cells were cultured for 24 hours and treated with the library compounds at two concentrations (1 and 10 μM) in RPMI 1640. In each assay plate, cells in 24 wells treated with 0.2% DMSO alone were used as controls. As a positive control, 1 μM MG132 was added to a single column of the assay plate. Following 12 hours of incubation, cells were fixed in 3% paraformaldehyde for 20 minutes, then washed with PBS and screened for localization of the PIR protein.

Microscope Automation and Image Processing:

WiScan™ Cell Imaging System (Idea Bio-Medical) was used for this screen [Paran Y et al., 2006, Methods Enzymol 414: 228-247]. The system is based on an IX71 microscope (Olympus), equipped with a fast laser AutoFocus device and an automated stage. Thirty-six fields were acquired from every well using a 60x/0.9 air objective, stored, and tiled into montages to detect consistent effects. Scoring of the nuclear translocation of the fluorescent PIR protein was carried out manually.

In Vitro Proteasome Activity Assay:

For measuring proteasome activity, purified 20S or 26S proteasomes prepared from rabbit muscles were incubated at a final concentration of 16 nM, with 100 μM fluorogenic 7-amido-4-methylcoumarin (AMC) tetrapeptide substrate Suc-LLVY-AMC (Bachem) and the stated concentration of the hit compounds in the presence of 100 μl of assay buffer (50 mM Hepes, 5 mM $MgCl_2$, 2 mM ATP and 1 mM DTT). The well-documented proteasomal inhibitor MG132 was used as a positive control, and an equivalent volume of solvent as a negative control. The time-dependent increase of hydrolyzed AMC groups was measured in a 96-well plate equilibrated to 37° C., using a Varioscan multi-well plate reader (Thermo Fisher Scientific, Inc.) in a kinetic mode, in which the recording intervals were set to 1 minute. The excitation wavelength was 370 nm; fluorescence emission was recorded at 465 nm.

Immunobloting:

H1299-PIR cells were lysed with radioimmune precipitation assay buffer (1% NP-40, 1% sodium deoxycholate, 0.1% SDS, 150 mM NaCl, 50 mM Tris, pH 8.0) containing a protease inhibitor cocktail from Roche Applied Science. Protein extracts were subjected to 8% SDS-PAGE, transferred to a nitrocellulose membrane (Whatman), and probed with monoclonal anti-p53 (DO1, Santa Cruz Biotechnology), anti-ubiquitin (Covance), anti-β-catenin (Sigma) and anti-β-tubulin (Sigma) primary antibodies.

For sub-cellular fractionation, cells were harvested and resuspended in ice-cold hypotonic lysis buffer [10 mM HEPES pH 7.9, 1.5 mM $MgCl_2$, 10 mM KCl, 1 mM DTT, supplemented with a complete protease inhibitor cocktail (Roche)], incubated on ice for 15 minutes, then NP40 was added, to a final concentration of 0.6%. The samples were vortexed for 10 seconds and immediately centrifuged at 12,000 g for 30 seconds. The supernatant (cytoplasmic fraction) was transferred to a fresh tube. The nuclei pellet was washed once with hypotonic lysis buffer, and lysed with SDS sample buffer (100 mM Tris-HCl pH 6.8, 2% SDS, 100 mm DTT, and 10% glycerol).

Cell Viability Assay:

The effect of each hit compound on cell viability was tested at 11 different concentrations, ranging from 0.1-100 μM. PIR cells were plated onto 384-well microplates for 24 hours, and then treated for 48 h with the library compounds. Cell viability was determined using the colorimetric AlamarBlue® (Invitrogen) viability assay, according to the manufacturer's instructions. Results are expressed as $GI_{50}$; namely, the compound concentration that reduces the AlamarBlue® score by 50%, compared to untreated controls.

Results

Figure 1:
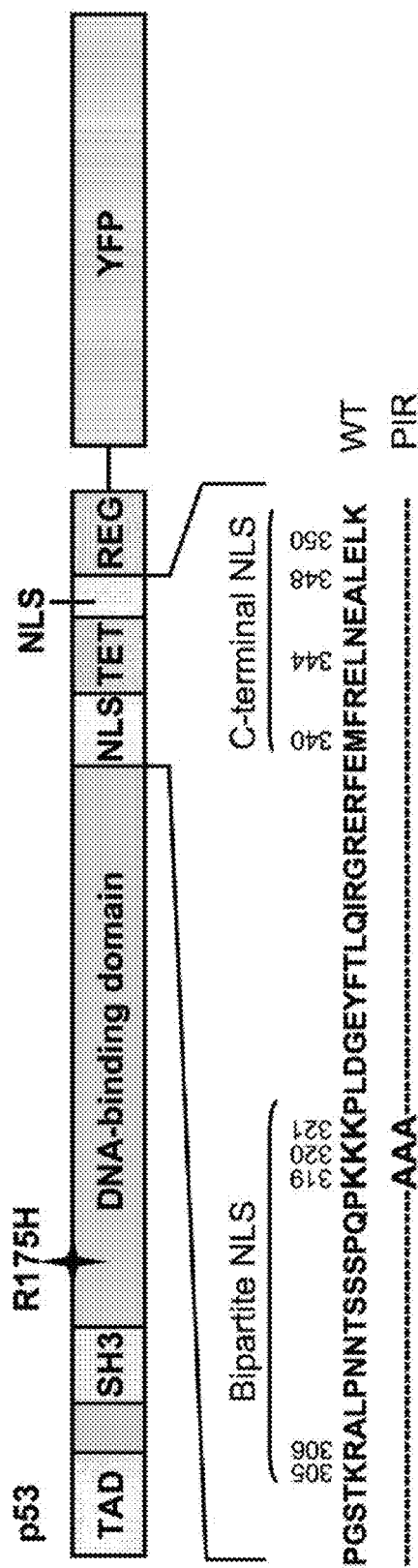
Figure 2:
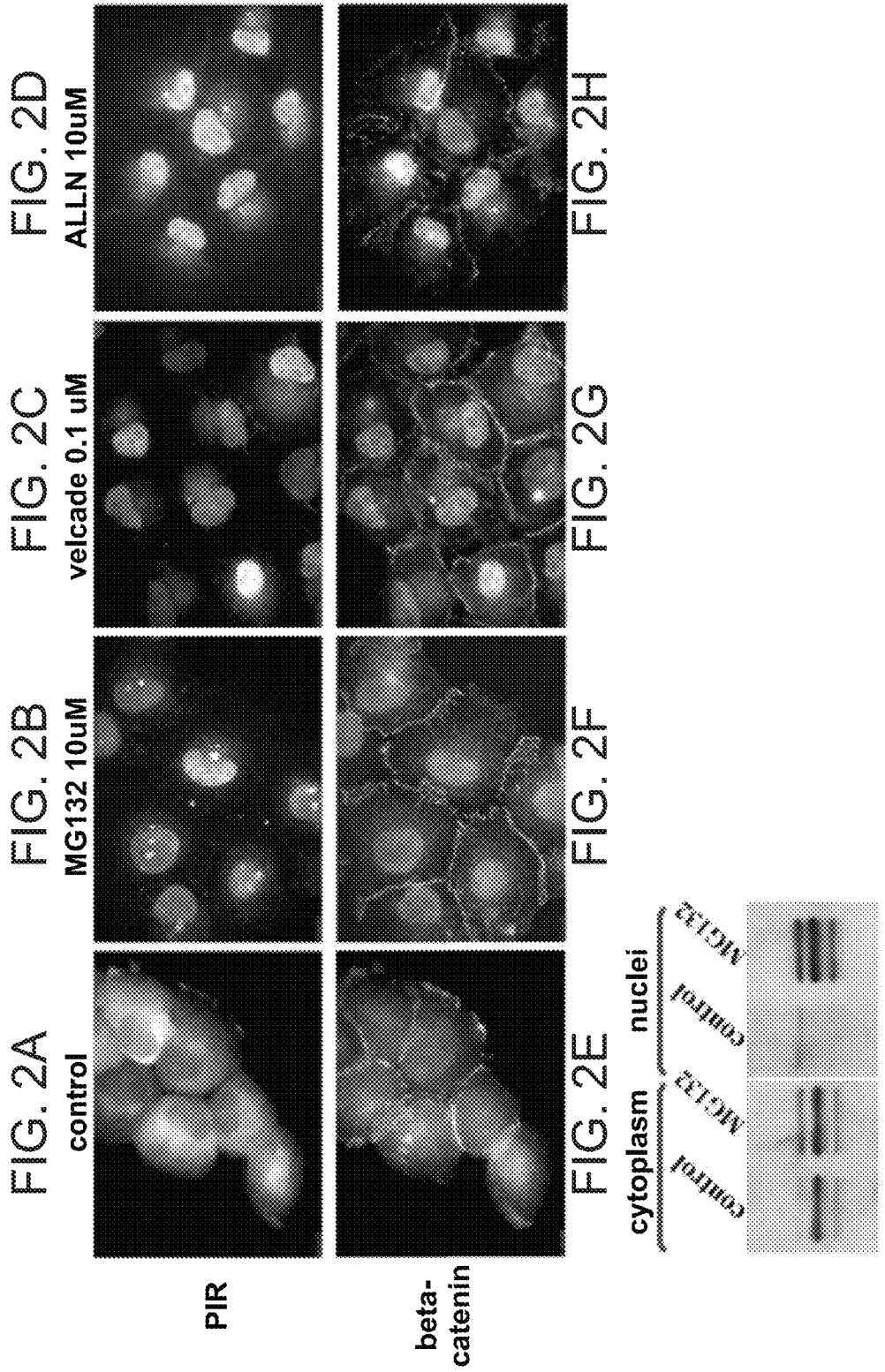
Figure 3:
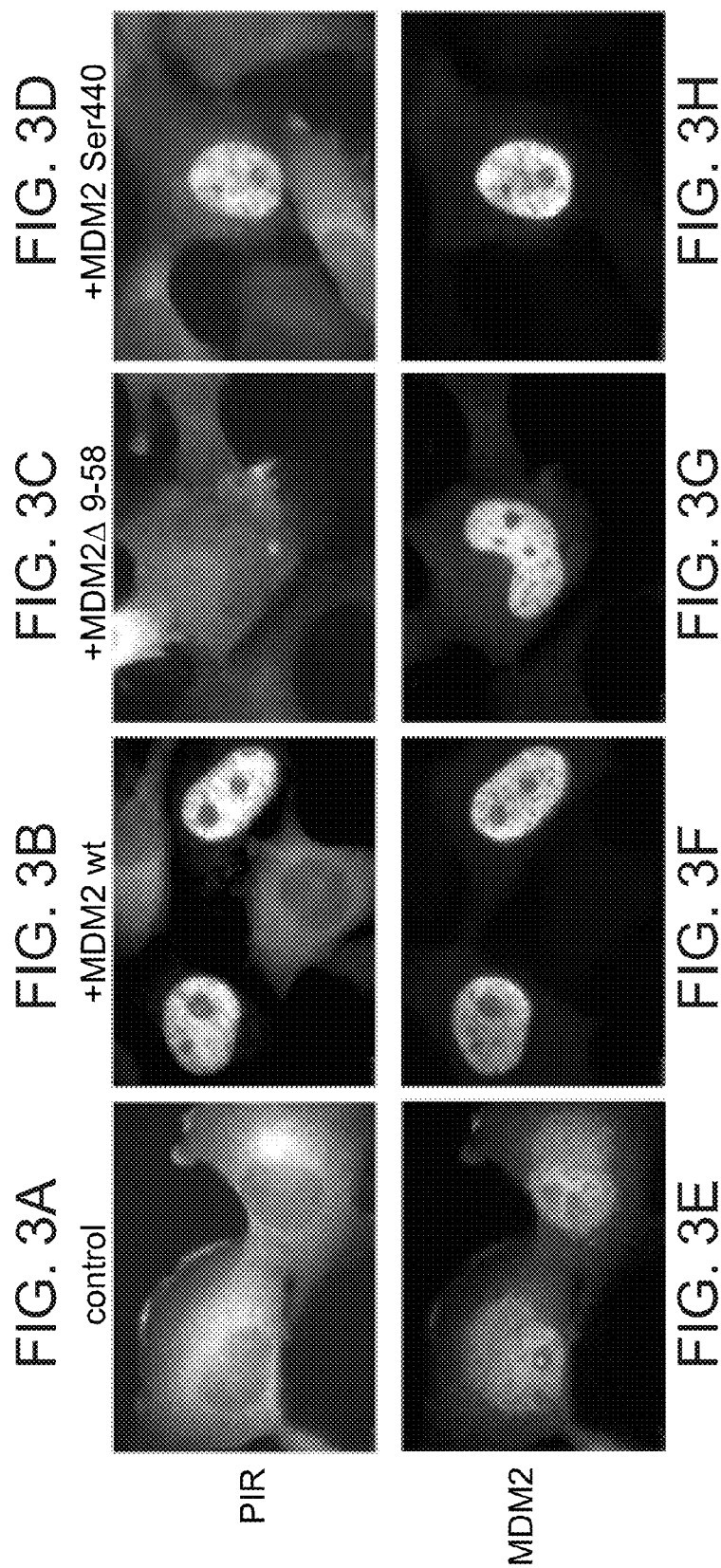
Figure 4:
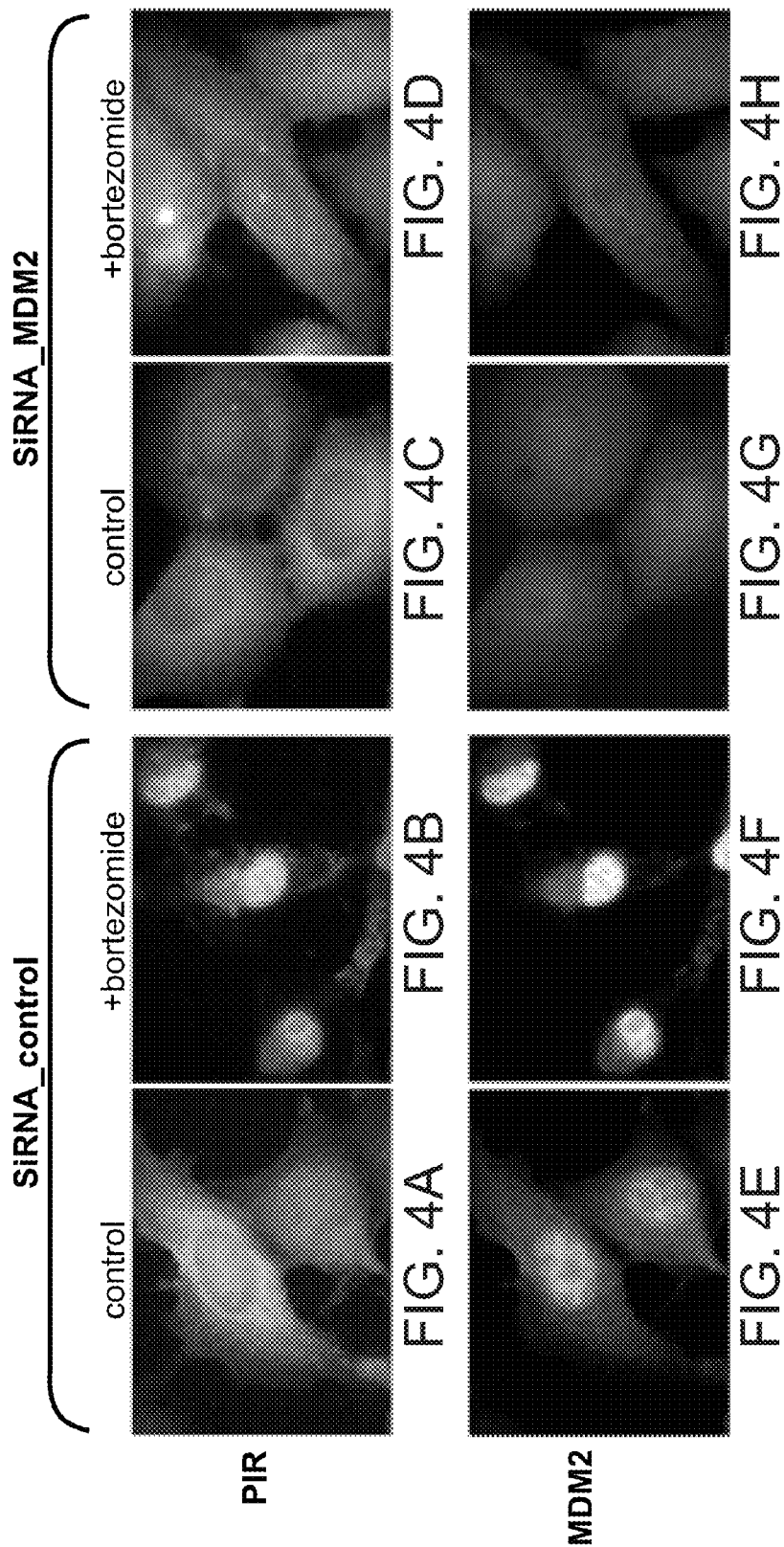

Development H1299-PIR Reporter Cell Line and its Application for Image-Based, High-Throughput Screening Assay for Proteasome Inhibitors As seen in FIG. 1, the PIR protein, used here for proteasome inhibitor screening, was constructed of yellow fluorescent protein (YFP) fused to the C-terminus of the human p53 R175H mutant. The cytoplasm-to-nucleus transport of this p53 mutant was attenuated by additional triple mutation in the bipartite NLS in which three consecutive lysine residues were replaced with alanines (K319A, K320A, and K321A), as described by O'Keefe et al [Mol Cell Biol 23: 6396-6405, 2003]. In agreement with previous reports, under normal cell culture conditions, this point mutation leads to cytoplasmic localization of the PIR protein in H1299 cells [O'Keefe et al., Mol Cell Biol 23: 6396-6405, 2003], confirming that the three basic residues at position 319-321 are indeed part of a nuclear localization signal. However, upon treatment with known proteasome inhibitors (e.g. MG132, Bortezomib and ALLN), PIR translocates into the nucleus in a manner reminiscent of p53 mutated in its NLS (FIGS. 2A-D). β-catenin, whose cellular levels are primarily regulated by the proteasome, underwent similar nuclear translocation in response to proteasome inhibition (FIGS. 2E-H), yet this was accompanied by significant stabilization and increase in its quantity unlike PIR, whose overall levels did not markedly change. To validate these results, the levels of PIR in the nuclear and cytoplasmic fractions of treated and control H1299-PIR cells were quantified using immunoblotting. This assay confirmed the microscopy-based observation, and pointed to a ~3-fold increase in the nuclear/cytoplasmic ratio of PIR, in response to MG132 treatment (FIG. 2I).

To assess the sensitivity of the PIR cell-based assay, H1299-PIR cells were incubated for 8 hours with different concentrations (0.01-10 μM) of known proteasome inhibitors (MG132 and Bortezomib). The cells were then fixed and scored for nuclear translocation of PIR. The score ($EC_{50}$) refers to the concentration of inhibitor needed to induce nuclear translocation of PIR in 50% of the treated cells. This test indicated that in our assay, the $EC_{50}$ values for MG132 and Bortezomib were 0.5 μM, and 0.05 μM, respectively. These values favorably compare with those reported for other detection systems, such as the commercial Living Colors HEK 293 ZsGreen Proteasome Sensor system (Clontech), which detects MG132 at 2.5 μM (after 20 hours of treatment using flow cytometry) [Andreatta C et al., Biotechniques 30: 656-660] or for the Ubi[G76V]-GFP-based reporter system (BioImage), in which the reported $EC_{50}$ value for MG-132 was approximately 1.0 μM [Dantuma et al, 2000 Nat Biotechnol 18: 538-543]. Thus, H1299-PIR cells appear to be sensitive reporters, capable of detecting the activity of proteasome inhibitors in a cell-based assay.

Nuclear Accumulation of Endogenous MDM2 in Response to Proteasome Inhibition is Responsible for PIR Nuclear Translocation To further characterize the mode of PIR nuclear translocation upon proteasome inhibition, the present inventors considered the possibility that proteasome-sensitive p53 binding proteins, are responsible for carrying PIR into the nucleus. Towards this end, MDM2, a p53 E3 ubiquitin ligase and a known target of proteasome-dependent degradation, was transfected into PIR cells, and its localization was assessed by immunofluorescence microscopy. As expected, endogenous MDM2 labeling in the PIR-H1299 cells was relatively faint and mostly nuclear while PIR was mainly localized to the cytoplasm (FIGS. 3A-H). In contrast, in the cells transfected with wild type MDM2, both the fluorescent PIR and MDM2 translocated to the nucleus. This suggests that MDM2 can transport NLS-deficient PIR from the cytoplasm into the nucleus, perhaps via the NLS of MDM2, consistently with previous studies suggesting that MDM2 can promote the nuclear import of ΔNLS p53. Interestingly, PIR remained cytoplasmic in cells over-expressing a mutated MDM2 lacking the p53 binding site (MDM2 Δ 9-58), suggesting that the interaction between the two proteins is needed for their cotranslocation to the nucleus. On the other hand, MDM2 mutant with point mutation that abolishes its E3 ubiquitin ligase function (MDM2 Ser440) induced PIR nuclear localization similar to the wild type molecule.

To check whether MDM2 expression is critical for PIR nuclear translocation, siRNA-mediated knockdown of MDM2 expression was performed in PIR-cells, and then treated the cells with proteasome inhibitors (FIGS. 4A-H). It was found that when MDM2 levels in the knocked-down cells were reduced, PIR remained cytoplasmic even following treatment with proteasome inhibitors, indicating that MDM2 is an essential player in the nuclear localization of NLS-deficient PIR.

Screening for Novel Proteasome Inhibitors in the Diversity Set of the NIH/NCI Chemical Library To assess the potential use of the cytoplasm-to-nucleus translocation of PIR in high-throughput, microscopy-based screening for novel proteasome inhibitors, 1,992 low molecular weight compounds comprising the NCI Diversity Set chemical library were tested. A flow chart depicting the screening procedure is shown in FIG. 5, and described in the Experimental Procedures. Following the initial automated screen, the images of the affected cells were inspected manually and a secondary screen was performed, in which hit compounds were tested at multiple concentrations, and directly compared to the well-established proteasome inhibitor MG132. This procedure resulted in the discovery of four compounds that induced nuclear translocation of PIR, indicating a hit rate of ~0.2%. As summarized in FIG. 6, all four compounds detected in the primary screen were confirmed by manual inspection.

Biochemical Validation of the Inhibitory Effects of the Hit Compounds

One characteristic outcome of proteasome inhibition is the accumulation of ubiquitinated proteins in the treated cells. To monitor the levels of ubiquitinated proteins that accumulated upon incubation with the novel inhibitors detected in the present screen, H1299-PIR cells were treated with each of the inhibitors for 6 hours, at doses comparable to those that were used in the screen. Following incubation, cell extracts were analyzed by Western blot, using anti-ubiquitin and anti-β-catenin antibodies. As shown in FIGS. 7A-B, accumulation of endogenous polyubiquitinated proteins, as well as elevated levels of β-catenin (a known target of the proteasome), at varying degrees, were caused by all four inhibitors, confirming their inhibitory effect on proteasomal degradation. The hit compounds NSC321206 (at a concentration of 0.15 μM) and NSC310551 (0.3 μM) were the most effective, demonstrating inhibitory activity comparable to that of 5 μM MG132. NSC99671 and NSC3907 (50 μM and 20 μM, respectively) displayed less of an inhibitory effect. It is noteworthy that the same concentrations that induced nuclear transport in the PIR assay, also resulted in accumulation of polyubiquitinated proteins and stabilization of β-catenin. Moreover, the potency of proteasomal inhibition, judged by these criteria, coincides nicely with the magnitude of the nuclear fluorescence signal detected in the PIR cell-based assay, upon inhibition with the different hit compounds.

To directly test the capacity of the four compounds to inhibit activity in mammalian proteasomes, an in vitro activity assay was performed in which the hit compounds were tested for their effects on the degradation of the model fluorogenic tetrapeptide LLVY-AMC by purified rabbit 26S proteasomes. As seen in FIG. 8, all four compounds inhibited proteasomal degradation to varying degrees. Both NSC310551 and NSC321206 showed levels of inhibition comparable to that of MG132, with NSC321206 being the most effective inhibitor. NSC99671 displayed a moderate inhibitory effect, and NSC3907 had only a minor effect. The low potency of NSC3907 in inhibiting the purified proteasome was consistent with previous findings, showing that this molecule (8-Quinolinol salicylate) can specifically inhibit the chymotryptic activity of the proteasome only in complex with intracellular copper. The fact that this compound was still picked up by the present screen reflects an advantage of this cell-based assay.

Effect of the Novel Proteasome Inhibitors on Cell Viability

Proteasome inhibitors are known to be particularly cytotoxic to malignant cells via multiple mechanisms. To directly test the effects of the new proteasome inhibitors discovered in this study on cell viability, PIR-expressing H1299 cells were treated for 48 hours with each of the four compounds, at a wide range of concentrations, ranging from 0.1 to 100 μM. The cells were then subjected to an Alamar Blue viability assay, which quantifies the number of metabolically active cells. As shown in FIG. 9, all four compounds affect cell viability, or inhibit the growth of PIR-H1299 cells (independent of the presence of PIR), at different concentrations. NSC3907 and NSC99671 exhibited a relatively weak growth inhibition effect, with $GI_{50}$ values of 47 μM and 96 μM, respectively, while NSC310551 and NSC321206 displayed a considerably stronger effect, with $GI_{50}$ values of 0.27 μM and 0.17 μM, respectively. For all proteasome inhibitors examined in this screen, there was a high correlation between proteasomal inhibitory activity and cell viability.

In view of previous reports, indicating that malignant cells are significantly more sensitive to proteasome inhibition than their normal counterparts, the present inventors compared the effect of the most effective inhibitory compound, NSC321206, toward normal breast epithelial cell line (MCF10A) and malignant breast carcinoma cells (MDM-MB-231) cell lines. As shown in FIG. 10 NSC321206 effectively eliminated all MDA-MB-231 cells at a concentration of 1 μM ($GI_{50}$ value of 0.4 μM), while the non-malignant breast epithelial cell line (MCF10A) were only partially affected, at a considerably higher concentration of this compound.

To gain insights into the effects of the present compounds on a wide variety of cells, published information on the effects of these compounds on the NCI-60 panel of human tumor cell lines used in the NCI Developmental Therapeutics Program (DTP) (http://dtpdotncidotnihdotgov) were explored. As seen in FIG. 11, the four hit compounds showed cytotoxic effects ($\log_{10} GI_{50} < -4.0$) against a variety of cell lines, whereas NSC321206 and NSC310551 demonstrated high cytotoxicity in vitro against all tested human cancer cell lines in the panel, with average negative $\log_{in} GI_{50}$ values of 7.2 and 6.6, respectively. The activity of NSC3907 was much lower, with a mean overall $-\log_{10} GI_{50}$ value of 5.3. NSC99671 was non-toxic for most of the lines (overall $-\log 10\ GI_{50}$ of 4.1). The most sensitive cell lines for all hit compounds were the leukemia cells, with overall $-\log_{10} GI_{50}$ equaling 7.73 for NSC321206, 7.028 for NSC310551, 6.249 for NSC3907, and 4.473 for NSC9967. These initial findings corroborate the present in vitro results, and directly demonstrate the use of the presently identified novel proteasomal inhibitors as potential therapeutic agents in cancer.

Characterization of the Possible Mode of Action of the Proteasome Inhibitor NSC321206, Discovered Using the PIR System To gain an insight into the inhibitory mechanism of NSC321206, a structural analysis of potential binding sites in the proteasome at large, and around its catalytic centers, in particular, was conducted. This survey addressed both the possibility that the $Cu^{++}$ ions play a role in the process, and the location of potential docking site for the entire NSC321206 molecule. A search for putative $Cu^{++}$ ion binding site (using CHED server) in the yeast 20S proteasome 3D structure revealed candidate binding sites for $Cu^{++}$ ions (without the organic ligand) on the outer surface of the α-ring, This was deemed irrelevant for inhibition. The search was then optimized, computationally, for the predicated 3D model of NSC321206. The optimized structure was similar to known crystallographic one. Once established these coordinates were used for searching for energetically favorable docking sites that may provide a structural bases for the observed inhibition of the Tryptic like (β2), Caspase like (β1) and Chymotrypsin like (β5) activities of the proteasome, that were found for NSC321206. The best 250 potential docking sites, located in the vicinity of each of these active sites were selected and grouped into clusters. A potential docking site for NSC321206 was identified. The site has a deep hydrophobic pocket and two Cys residues positioned in the ideal conformation with regards to the Cu atom of the inhibitor (FIGS. 12A-B).

DISCUSSION

Presently, few approaches for the high-throughput discovery of proteasome inhibitors exist, those that do, are mostly based on the use of biochemical techniques. Cell-based/image-based assays enables evaluation of potential proteasomal inhibitors that may not be detected using purified proteasomes and have several other advantages such as demonstrating that active compounds are cell-permeable and are sensitive to effects at multiple targets and nodes within a given pathway, as opposed to a strict cell-free assay that focuses on one particular target, such as degradation of a particular substrate by a purified proteasome. The main motivation directing the development of PIR was to establish a method enabling the assessment of proteasomal inhibition in a cellular context, based on the unequivocal translocation of a fluorescent reporter protein from the cytoplasm to the nucleus upon proteasomal inhibition, without grossly affecting its overall levels. This approach was found to be highly specific, with essentially no false positives, in contrast to existing cell-based screens for proteasomal inhibitors that monitor the accumulation of fluorescent signals from direct proteasomal substrates, that appear to be sensitive to autofluorescence and to the fluorescence-quenching effects of the screening molecules, as well as to variations in cell geometry, some of which may be induced, directly or indirectly, by proteasomal inhibition.

The design of the PIR reporter protein is based on a p53 R175H mutant which, in contrast to the short-lived, WT p53, has a significantly longer half-life (several hours), presumably due to its reduced susceptibility to proteasomal degradation. As a result, the overall concentration of PIR in cells is only marginally affected by treatment with proteasomal inhibitors such as MG132 (FIG. 2I). In the PIR assay, monitoring proteasomal inhibition is based on intracellular translocation of the reporter protein from the cytoplasm to the nucleus, in response to proteasomal inhibition. It is noteworthy that PIR was found to be particularly suitable for high throughput screening for proteasomal inhibitors, due to the unambiguous quantification of nuclear vs. cytoplasmic fluorescence.

In conclusion, the novel cell-based screen described here appears to be a robust and highly sensitive tool for the identification on new proteasome inhibitors. It is based on the stabilized MDM2-dependent accumulation of the PIR molecule in the nucleus, and is compatible with microscopy-based high throughput screening technology.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of identifying a proteasome inhibitor, the method comprising:
   (a) contacting a candidate inhibitor with a population of cells which express an isolated polypeptide comprising a p53 amino acid sequence, having a different cellular location in a presence or absence or, a proteasome inhibitor, the polypeptide being linked to a detectable moiety; and
   (b) analyzing a cellular location of said polypeptide in said population of cells, wherein a change in localization of said polypeptide is indicative of said candidate inhibitor being a proteasome inhibitor.

2. The method of claim 1, wherein the isolated polypeptide comprises an amino acid sequence as set forth by SEQ ID NO: 3.

3. The method of claim 1, wherein the isolated polypeptide comprises an amino acid sequence as set forth by SEQ ID NO: 6.

4. The method of claim 1, wherein the isolated polypeptide comprises a nuclear location in a presence of said proteasome inhibitor and a cytoplasmic location in an absence of said proteasome inhibitor.

* * * * *